US009296986B2

(12) United States Patent
Jones et al.

(10) Patent No.: US 9,296,986 B2
(45) Date of Patent: *Mar. 29, 2016

(54) SYSTEM FOR THE REDUCTION OF WATER CONTAMINATION

(75) Inventors: Robert Gavin Jones, Huntsville, TX (US); Gordon Alf Plishker, The Woodlands, TX (US)

(73) Assignee: Sam Houston State University, Huntsville, TX (US)

( * ) Notice: Subject to any disclaimer, the term of this patent is extended or adjusted under 35 U.S.C. 154(b) by 1438 days.

This patent is subject to a terminal disclaimer.

(21) Appl. No.: 13/032,408

(22) Filed: Feb. 22, 2011

(65) Prior Publication Data

US 2011/0233125 A1     Sep. 29, 2011

Related U.S. Application Data

(63) Continuation of application No. 11/367,762, filed on Mar. 3, 2006, now abandoned.

(51) Int. Cl.
| | | |
|---|---|---|
| *C12N 1/20* | (2006.01) | |
| *C12N 11/16* | (2006.01) | |
| *C12P 39/00* | (2006.01) | |
| *C02F 3/10* | (2006.01) | |
| *C02F 3/34* | (2006.01) | |

(52) U.S. Cl.
CPC . *C12N 1/20* (2013.01); *C02F 3/108* (2013.01); *C02F 3/341* (2013.01); *C02F 3/348* (2013.01); *C12N 11/16* (2013.01); *C12P 39/00* (2013.01); *Y02W 10/15* (2015.05)

(58) Field of Classification Search
CPC ...... C02F 3/341; C02F 3/34; C02F 2209/005; C02F 2209/22; C02F 2209/40; C02F 2209/42; C02F 3/006; C02F 3/348; C02F 3/108; C02F 2203/002; C02F 2209/06; C02F 2203/008; C02F 2103/10; C02F 2203/004; C02F 2209/04; C12N 9/16; C12N 15/8242; C12N 15/8247; C12N 9/18; C12N 9/20; C12N 15/52; C12N 15/8243; C12N 9/248; C12N 9/88; C12N 15/1137; C12N 15/8246; C12N 15/8255; C12N 1/20; C12N 2310/11; C12N 2310/14; C12N 9/005
See application file for complete search history.

(56) References Cited

U.S. PATENT DOCUMENTS

| | | |
|---|---|---|
| 4,009,098 A | 2/1977 | Jeris |
| 4,085,041 A | 4/1978 | Fullerton et al. |
| 4,696,901 A | 9/1987 | Robertson et al. |
| 4,994,391 A | 2/1991 | Hoffmann |
| 5,217,616 A | 6/1993 | Sanyal et al. |
| 5,388,316 A | 2/1995 | Maclaren |
| 5,599,451 A | 2/1997 | Guiot |
| 5,744,337 A | 4/1998 | Price et al. |
| 5,756,304 A | 5/1998 | Jovanovich |
| 5,912,398 A | 6/1999 | Goldstein et al. |
| 5,928,514 A | 7/1999 | Gothreaux |
| 5,976,377 A | 11/1999 | Hyfantis, Jr. et al. |
| 6,013,511 A | 1/2000 | Diels et al. |
| 6,039,875 A | 3/2000 | Christiansen et al. |
| 6,245,237 B1 | 6/2001 | Blough et al. |
| 6,335,191 B1 | 1/2002 | Kiplinger et al. |
| 6,342,159 B1 | 1/2002 | Caplan et al. |
| 6,461,500 B1 | 10/2002 | Hoage et al. |
| 6,719,902 B1 | 4/2004 | Alvarez et al. |
| 6,758,633 B2 | 7/2004 | Yen |
| 6,790,355 B2 | 9/2004 | Shaffer et al. |
| 6,790,365 B2 | 9/2004 | Hirai |
| 6,841,515 B2 | 1/2005 | Burnham |
| 6,849,445 B2 | 2/2005 | Fayolle et al. |
| 6,861,245 B1 | 3/2005 | Smit |
| 6,921,477 B2 | 7/2005 | Wilhelm |
| 6,989,102 B1 | 1/2006 | Park et al. |
| 7,022,234 B2 | 4/2006 | Shaffer et al. |
| 7,175,766 B2 | 2/2007 | Kim et al. |
| 7,189,281 B2 | 3/2007 | Kim |

(Continued)

FOREIGN PATENT DOCUMENTS

| | | |
|---|---|---|
| EP | 0745562 | 12/1996 |
| JP | 05-192677 | 8/1993 |

(Continued)

OTHER PUBLICATIONS

"Aeration of Animal Wastes Newman Environmental Solutions, Inc. (NESi) Greenville, N.C.," available on the Advanced Aeration, Inc. website at http://www.advancedaeration.com. Published 1998.

"Apex Innovation Test Development of Vacuum Bubble® Aerator for Remediation of Petroleum Contaminated Sites," available on the Advanced Aeration, Inc. website at http://www.advancedaeration.com. Published 2004.

"Bioremediation of Contaminated Soil, Groundwater, and Wastewater" from the Environmental Biotechnology Laboratory website at http://www.nies.go.jp/kenko/biotech/research/biore Published 2002.

(Continued)

*Primary Examiner* — Debbie K Ware
(74) *Attorney, Agent, or Firm* — Meyertons, Hood, Kivlin, Kowert & Goetzel, P.C.; Eric B. Meyertons

(57) ABSTRACT

In some embodiments, a system may reduce contaminants in water. A system may include a biofilm in a container. The biofilm may be formed from one or more bacteria coupled to one or more substrates. The bacteria may be selected to maximize the reduction of contaminants in water. The system may include one or more bacteria generators to provide bacteria to the biofilm and/or one or more air sources to provide an air bubble stream to the container and/or the bacteria generator. In some embodiments, bacteria may be preserved in a starvation phase. Bacteria may be incubated until they reach a starvation phase. The bacteria may then be preserved as beads or immobilized on a substrate. The preserved bacteria may be used in a system for the reduction of contaminants in water.

14 Claims, 11 Drawing Sheets

(56) References Cited

U.S. PATENT DOCUMENTS

| | | | |
|---|---|---|---|
| 7,326,344 | B2 | 2/2008 | Cotoras Tadic et al. |
| 7,431,832 | B2 * | 10/2008 | Plishker et al. ............... 210/150 |
| 7,485,224 | B2 * | 2/2009 | Jones et al. ................... 210/241 |
| 2001/0011643 | A1 | 8/2001 | Newton et al. |
| 2004/0175407 | A1 | 9/2004 | McDaniel |
| 2005/0150829 | A1 | 7/2005 | Chen |
| 2006/0163154 | A1 | 7/2006 | Tay et al. |
| 2007/0205148 | A1 | 9/2007 | Jones et al. |
| 2007/0205149 | A1 | 9/2007 | Jones et al. |
| 2007/0205150 | A1 | 9/2007 | Jones et al. |
| 2007/0205151 | A1 | 9/2007 | Plishker et al. |
| 2007/0205157 | A1 | 9/2007 | Jones et al. |
| 2007/0207534 | A1 | 9/2007 | Jones et al. |
| 2011/0233125 | A1 | 9/2011 | Jones et al. |

FOREIGN PATENT DOCUMENTS

| | | |
|---|---|---|
| JP | 07-251191 | 10/1995 |
| WO | 9218609 | 10/1992 |
| WO | 2004052795 | 6/2004 |

OTHER PUBLICATIONS

Bramucci et al. "Bacterial diversity in an industrial wastewater bioreactor" Appl. Biotechnol. (2003) 62:594-600.
Goode et al. "Effect of Calcium on Moving-Bed Biofilm Reactor Biofilms" Water Environment Research, vol. 83, No. 3, p. 220-232 (2011).
Hoage et al. "Innovation Aeration Retrofit of Existing Failed Septic Systems around Lake Livingston, Texas." Advanced Aeration, Inc. website. Published 2004.
Hoage et al. "Aeration Pretreatment for Commercial Restaurants." Advanced Aeration, Inc. website. Published 2006.
Hockin et al. "Linked Redox Precipitation of Sulfur and Selenium under Anaerobic Conditions by Sulfate-Reducing Bacterial Biofilms" Applied and Environmental Microbiology (2003) vol. 69, No. 12, p. 7063 7072.
Ibanez et al. "Potential of protonated alginate beads for heavy metals uptake" Hydrometallugry, 2002, vol. 64, pp. 89-99.
Jodra et al. "Ion Exchange Selectivies of calcium alginate gels for heavy metals," Water Sci. Technol., vol. 43, No. 2, 2001, pp. 237-244 (Abstract).
Kaprelyants et al. "Dormancy in Stationary-Phase Cultures of Micrococcus luteus: Flow Cytometric Analysis of Starvation and Resuscitation." Applied and Environmental Microbiology, Oct. 1993, vol. 59, No. 10, p. 3187-3196.
Lewandowski et al. "Heavy Metals Removal from Contaminated Water Solutions," HSRC The Great Plains/Rocky Mountain Hazardous Substance Research Center Jan. 25, 2005.
Lichtenberg et al. "A kinetic approach to bacterial adherence to hydrocarbon" Journal of Microbiological Methods, vol. 4, Nov. 1995, pp. 141-146.
Lowry "Comparison of Four Treatment Methods for the Removal of Lipids and Food Waste in a Grease Trap Environment." Advanced Aeration, Inc. website. Published 2004.
Nelson "Struvite precipitation in anaerobic swine lagoon liquid: effect of pH and Mg:P ratio and determination of rate constant." Bioresource Technology 89 (2003) 229-236.
Ogden et al. "Investigating the use of biosorption to treat copper CMP wastewater," www.micromagazine.com, Jul./Aug. 2001.
Okazaki et al. "Development of poly(vinyl alcohol) hydrogel for waste water cleaning. II. Treatment of N,N-dimethylformamide in waste water with poly(vinyl alcohol) gel with immobilized microorganisms" J. of Applied Polymer Science, vol. 58, 2243-2249 (1995), (Abstract).
Roheim "Low Cost Automated on Site Systems for Growing and Dispensing Vegetative Bacteria," available on the ECOBionics website. Published Jan. 20, 2005.
Uemoto et al. "Distribution of Nitrosomonas europaea and Paracoccus denitrificans Immobilized in Tubular Polymeric Gel for Nitrogen Removal" Applied and Environmental Microbiology, Feb. 2000, p. 816-819, vol. 66, No. 2.
Vyrides "Effect of fluctuations in salinity on anaerobic biomass and production of soluble microbial products (SMPs)" Biodegradation (2009) 20:165-175.
PCT Application No. PCT/US2007/063317, Search Report, Mailed Jan. 18, 2008.
PCT Application No. PCT/US2007/063317, Written Opinion, Mailed Jan. 18, 2008.
PCT Application No. PCT/US2007/063317, IPRP, Mailed Sep. 9, 2008.
PCT Application No. PCT/US2012/039373, Search Report, Mailed Dec. 10, 2012.
PCT Application No. PCT/US2012/039384, Search Report, Mailed Dec. 10, 2012.
PCT Application No. PCT/US2012/039393, Search Report, Mailed Dec. 10, 2012.
PCT Application No. PCT/US2012/039400, Search Report, Mailed Dec. 10, 2012.
Office Action issued on Jan. 14, 2008 for U.S. Appl. No. 11/368,282.
Office Action issued on Jan. 16, 2007 for U.S. Appl. No. 11/368,320.
Office Action issued on Jun. 21, 2007 for U.S. Appl. No. 11/368,320.
Office Action issued on Jan. 10, 2008 for U.S. Appl. No. 11/368,320.
Office Action issued on Oct. 15, 2008 for U.S. Appl. No. 11/367,762.
Office Action issued on May 4, 2009 for U.S. Appl. No. 11/367,762.
Office Action issued on Dec. 1, 2009 for U.S. Appl. No. 11/367,762.
Office Action issued on Aug. 20, 2010 for U.S. Appl. No. 11/367,762.
Office Action issued on Jan. 2, 2009 for U.S. Appl. No. 11/368,330.
Office Action issued on Jun. 17, 2009 for U.S. Appl. No. 11/368,330.
Office Action issued on Nov. 18, 2009 for U.S. Appl. No. 11/368,330.
Office Action issued on Jan. 12, 2009 for U.S. Appl. No. 11/368,319.
Office Action issued on May 26, 2009 for U.S. Appl. No. 11/368,319.
Office Action issued on Sep. 22, 2009 for U.S. Appl. No. 11/368,319.

* cited by examiner

US 9,296,986 B2

SYSTEM FOR THE REDUCTION OF WATER CONTAMINATION

PRIORITY

This application is a continuation of U.S. patent application Ser. No. 11/367,792, entitled "SYSTEMS AND METHODS OF CREATING A BIOFILM FOR THE REDUCTION OF WATER CONTAMINATION", filed Mar. 3, 2006, which is hereby incorporated by reference in the entirety as though fully and completely set forth herein.

STATEMENT REGARDING FEDERALLY SPONSORED RESEARCH OR DEVELOPMENT

This invention was made with Government support under Contract # F41624-02-Z-9000 awarded by the Air Force AFIOH TRIES Collaborative Water/Wastewater Treatment Technology Project. The Government has certain rights to this invention.

BACKGROUND

1. Field of the Invention

The present invention relates to systems and methods for treating water and preserving bacteria. More particularly, the invention relates to the reduction of contaminants from wastewater and preserving bacteria in a starvation phase.

2. Description of Related Art

Fluidized bed bioreactors are often used to treat wastewater. Granular media containing bacteria may be positioned in a water column and fluidization may be obtained by liquid recirculation or by external gas fed into the reactor. A biomass may form on the granular media. Wastewater may be batch processed by the biomass. Some new wastewater treatment systems rely on activated sludge from operational wastewater treatment systems to form a biofloc or biomass. However, formation of the biofloc or biomass from the sludge may be time consuming and may not allow customization for specific wastewater contaminants. In addition, as bacteria in a biofloc or biomass fall off of the mass and/or die, a system to replenish specific strains of bacteria in the biofloc may not exist.

Bacteria are usually preserved in the logarithmic growth stage since the growth rate of bacteria exceeds the death rate during this stage. The bacteria are usually preserved by lyophilization or by forming compression tablets. These techniques are time consuming, inefficient, prone to contamination, and/or not cost effective.

SUMMARY

In some embodiments, a system for the reduction of contaminants in water may include one or more containers that include bacteria coupled to one or more substrates. In an embodiment, a biofilm may form in the container that includes bacteria coupled to one or more substrates. The system may include one or more bacteria generators that provide bacteria to a container. The system may also include one or more air sources to provide air, as for example, an air bubble stream. In an embodiment, an air source may be coupled to containers and/or bacteria generators.

In some embodiments, the system may be used to process and/or reduce the amount of contaminants in wastewater. In certain embodiments, when a system for the reduction of contaminants has foaming, one or more hydrophobic substrates may be added to at least one of the containers with foaming. The bacteria may couple to the substrate. When the bacteria couple to the substrate, foaming may be reduced or eliminated.

In some embodiments, a biofilm may include one or more primary adherer bacteria and one or more secondary adherer bacteria. Primary adherer bacteria may couple to one or more substrates. In certain embodiments, primary adherer bacteria may also couple to one or more other bacteria. Secondary adherer bacteria may couple to one or more bacteria. Primary adherer bacteria and/or secondary adherer bacteria may be capable of reducing contaminants in water. In an embodiment, at least one of the secondary adherer bacteria may reduce a greater amount of at least one of the contaminants in water than at least one of the primary adherer bacteria.

In various embodiments, bacteria may be preserved for later use and/or for use in systems for the reduction of contamination. Bacteria in a container, such as bacteria generator, may incubate and/or grow until at least a portion of the bacteria enters the starvation phase. The bacteria then may be preserved. In some embodiments, bacteria may be preserved as bacteria-alginate beads and/or immobilized on hydrophobic substrates.

In some embodiments, when forming bacteria-alginate beads, bacteria may be added to alginate, such as sodium alginate. The bacteria-alginate mixture or solution is added to a solution comprising metal ions and particles may form. In other embodiments, when forming bacteria immobilized on hydrophobic substrates, bacteria may be incubated on a hydrophobic substrate. The hydrophobic substrate containing bacteria may be then added to a solution that includes alginate. The alginate may penetrate the hydrophobic substrate. Next, the hydrophobic substrate is added to a solution comprising metal ions and the bacteria may be immobilized on the hydrophobic substrate.

BRIEF DESCRIPTION OF THE DRAWINGS

Features and advantages of the methods and apparatus of the present invention will be more fully appreciated by reference to the following detailed description of presently preferred but nonetheless illustrative embodiments in accordance with the present invention when taken in conjunction with the accompanying drawings in which.

Figure 1:
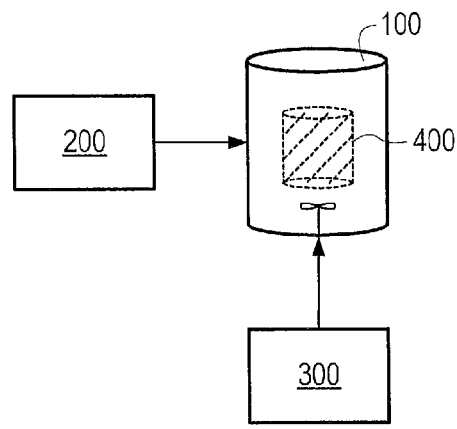
FIG. 1 depicts an embodiment of a system for the reduction of contaminants in water.

While the invention is susceptible to various modifications and alternative forms, specific embodiments thereof are shown by way of example in the drawings and will herein be described in detail. The drawings may not be to scale. It should be understood that the drawings and detailed description thereto are not intended to limit the invention to the particular form disclosed, but to the contrary, the intention is to cover all modifications, equivalents and alternatives falling within the spirit and scope of the present invention as defined by the appended claims.

DETAILED DESCRIPTION OF EMBODIMENTS

Herein are described systems and methods for the reduction of contaminants in water. The system may process industrial wastewater, municipal wastewater, and/or water in septic or sewer systems. The system may process wastewater using bacteria to reduce the amount of contaminants in the wastewater. The bacteria may form a biofilm on a substrate.

Unless defined otherwise, all technical and scientific terms used herein have the same meaning as commonly understood by one of ordinary skill in the art. In the context of this application, the following terms are defined as:

An "air source" refers to a device capable of providing air or other gasses to a liquid.

"Bacteria" refers to any member of the Bacteria Domain.

A "bacteria generator" refers to a device capable of allowing one or more bacteria to grow and/or reproduce.

A "biofilm" refers to a collection of more than one bacteria coupled together.

A "contaminant" refers to any unwanted substance or compound.

"Coupling" refers to attaching, bonding, adhering, welding, or a direct connection of two or more objects.

"Enteric bacteria" refers to bacteria that are found in the digestive tract of animals.

A "filament" refers to a portion of a bacterium that extends from the body of the bacterium.

"Foam" refers to an aggregate of gas bubbles formed in a liquid or solid. Foam in a liquid may suspend solid particles and inhibit settling of the solid particles to a bottom of a container.

A "footprint" refers to an area on a surface an object occupies.

"Gene-up regulation" refers to activation of a property of a bacterium after the bacterium couples to a substrate. For example, a gene may be activated, protein synthesis may occur, and/or metabolic activity may be increased or decreased during gene-up regulation of a bacterium.

A "heterotroph" is an organism that requires organic compounds as a carbon source for growth and development. A heterotroph is not able to use carbon dioxide as its sole carbon source.

A "hydrophobic substrate" refers to a substrate that does not form hydrogen bonds with itself, which causes it to at least partially repel water.

An "oligotroph" refers to an organism that can live in environments with a carbon concentration of less than 1 ppm.

An "organic compound" refers to a compound that includes carbon. An organic compound may include elements other than carbon, such as oxygen, nitrogen, sulfur, and/or metals.

"Primary adherer bacteria" refers to any member of the Bacteria Domain capable of coupling to a substrate and/or other bacteria.

"Stagnant regions" refers to areas that are not substantially flowing.

"Secondary adherer bacteria" refers to any member of the Bacteria Domain capable of coupling to another bacteria but incapable of coupling to a substrate.

"Reducing contaminants in water" refers to reducing an amount of contaminant in water, degrading contaminants, altering contaminants (e.g., altering a metal contaminant such that it precipitates), absorbing contaminants, immobilizing contaminants, and/or removing one or more contaminants from water.

"Wastewater" refers to a fluid comprising one or more contaminants.

In some embodiments, a system for the reduction of contaminants in water may include one or more, one or more containers 100, bacteria generators 200, and/or one or more air sources 300, as depicted in FIG. 1. One or more bacteria generators 200 and/or air sources 300 may be coupled to a container 100. One or more air sources 300 may be coupled to bacteria generator 200. One or more substrates 400 may be positioned in a container 100. Bacteria may be coupled to the substrate 400 and/or other bacteria in a container 100 to form a biofilm in the container. In an embodiment, bacteria may be provided to a container 100 by one or more bacteria generators 200 and/or an air bubble stream may be provided by one or more air sources 300.

In some embodiments, the system may include one or more containers. A container may be formed of plastic, metal, and/or other materials. A container may include one or more coatings. A coating may inhibit corrosion and/or facilitate removal of solids from a container. For example, a container may have a polytetrafluoride coating to inhibit corrosion and to inhibit solids from adhering to the container.

In some embodiments, a footprint of a container may be substantially square, substantially circular, substantially oval, substantially rectangular, and/or irregularly shaped. A container may have a shape configured to minimize stagnant regions in the container. In certain embodiments, the shape of the inner surface of the container may minimize stagnant regions in the container during mixing. The inner surfaces of a container may be rounded instead of meeting at an edge. For example, an inner surface of a container may have a shape substantially similar to an oval or a circle to minimize the presence of stagnant regions in the container, during use. In an embodiment, a container may have a shape in which substantially all of the liquid in one or more of the containers circulates when mixed with a stirrer during use.

In an embodiment, a bottom surface of a container may have a shape to collect bacteria or other solid materials in the container that sink to a bottom of the container and/or minimize the affect of solids sinking to a bottom surface on flow within the container. For example, a bottom surface of a container may be tapered, convex, or substantially conically shaped. A bottom region of a container may have approximately 10% to approximately 35% grade from horizontal. In an embodiment, a bottom region of a container may have approximately 23% to approximately 27% grade from horizontal.

In some embodiments, a conical bottom or tapered bottom region of a container may facilitate the removal of solids at the bottom of the container. As solids from the wastewater and/or biofilm sink to a bottom of a container, the solids may collect and inhibit contact of contaminants in wastewater with at least a portion of the biofilm. If a bottom surface of a container is tapered, convex, or substantially conical, then solids may collect in the bottom region of the container without substantially affecting contact between contaminants in the wastewater in the container and the bacteria of the biofilm.

In certain embodiments, a container with an elliptical inner surface cross-section area may be used in the system. Using a container with an elliptical inner surface cross-sectional area may allow a height of the container to be reduced while maintaining a similar capacity to a circular inner surface cross-sectional area container. In an embodiment, a container may have a length that is at least approximately 34% greater than its width and/or at least approximately 39% greater than its height. In another embodiment, the length of a container may be at least 22% greater than the height of the container with a bottom region that is tapered.

In some embodiments, a container may have a shape that allows enhanced use of the top surface of a platform. It may be desirable to utilize container with a footprint that maximizes area used on a surface of a platform. For example, if a platform has a rectangular top surface, a footprint and/or inner surface of a container may be oval or oblong to maximize an area on the top surface of a platform that the container utilizes and minimizing stagnant areas in the container. An area of a footprint of a container may be at least three-fourths the area of a top surface of a platform.

In an embodiment, a bottom surface of a container may have a shape to collect bacteria or other solid materials in the container that sink to the bottom of the container. A bottom surface of a container may have a shape such that when solids sinking to the bottom surface, fluid flow proximate the substrate in the container is not substantially inhibited. For example, a bottom surface of a container may be tapered, convex, or substantially conically shaped. As solids from the wastewater and/or biofilm sink to a bottom of a container, the solids may collect and inhibit contact of contaminants in wastewater with at least a portion of the biofilm. If a bottom surface of a container is tapered, convex, or substantially conical, then solids may collect in the bottom region of the container without substantially inhibiting contact between contaminants in the wastewater in the container and the bacteria of the biofilm.

A container may include one or more stirrers to agitate fluids and/or gasses in the container. One or more stirrers may be positioned to reduce dead mixing zones in the container. For example, a container with an oval cross-sectional area may include two stirrers approximately equally spaced across a bottom surface to inhibit areas of fluid stagnation the container.

In some embodiments, a container may include one or more inlets for wastewater streams, air bubble streams, and/or bacteria. A container may include one or more outlets for removal of fluids and/or solids from the container.

In some embodiments, filters may be coupled to inlets and/or outlets. A filter may be coupled to an inlet to remove and/or break apart large solids. A filter may be coupled to an outlet to prevent solids such as waste solids, bacteria, and/or particulate matter from flowing out of the container. In an embodiment, a filter may inhibit contaminants from water flowing out of the container. For example, filter paper or an activated carbon filter may be coupled to an outlet to remove contaminants from a stream flowing out of the container.

In some embodiments, a filter comprising activated carbon, such as a granulated activated carbon filter, may be coupled to an outlet of a container. An activated carbon filter may remove organic compounds and/or metal ions. The activated carbon filter may remove fine particles and/or bacteria from fluid flowing out of a container.

In certain embodiments, an electrocoagulation system may be coupled to inlets and/or outlets. An electrocoagulation system may be used prior to allowing fluid to enter a container comprising a biofilm and/or after allowing fluid to leave a container that includes a biofilm. The electrocoagulation system may cause compounds to precipitate and float to a top or bottom surface of a container for removal. In an embodiment, an electrocoagulation system may charge ions in a fluid. The charged ions may bind to oppositely charged ions and form a precipitate. Then the precipitates may float to a top surface or sink to a bottom surface of a container for removal from the fluid. In an embodiment the precipitates may be filtered out of the fluid.

Figure 2:
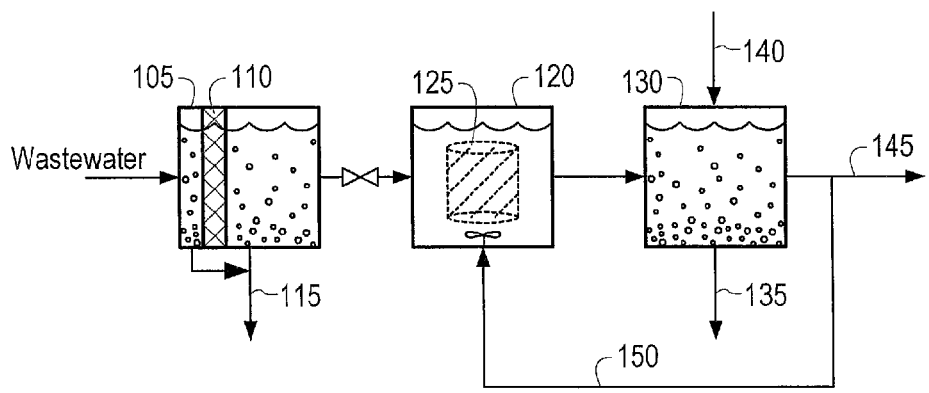
FIG. 2 depicts an embodiment of a system that includes settling containers for the reduction of contaminants in water.

One or more of the containers may be settling container. As depicted in FIG. 2, the system for reduction of contaminants may include one or more settling containers coupled to one or more other containers. A first settling container 105 may include a filter 110 that retains and/or break up large solids. The first settling container 105 may allow solids in wastewater entering the settling container to settle to a bottom of the settling container and be removed via a drain 115. Wastewater from the settling container 105 may be introduced into a container 120 containing bacteria 125 using a valve, such as a variable time release float valve. The container 120 may include one or more bacteria 125 that reduce contamination in the wastewater. In an embodiment, a second settling container 130 may be coupled to the container 120 containing bacteria 125 such that processed water may flow from the container that includes bacteria to the second settling container, in which solids from the container with bacteria may settle and may be removed via a drain 135. A disinfectant, such as chlorine 140 may also be added to the water in the second settling container 130. Water with substantially less contamination than the wastewater entering the first settling container may exit the second settling container via one or more outlets 145. In certain embodiments, water exiting the second settling container may be recycled through a recycle line 150 into the container 120 containing bacteria 125 until a desired level of reduction of contamination is achieved.

In some embodiments, one or more substrates may be positioned in a container. A substrate may be a structure on which a biofilm grows in a container. A substrate may be fixed to the container and/or removable from the container.

A substrate may be formed of plastic such as polypropylene or Kevlar®, metal, natural fibers such as cotton, other materials, or combinations thereof. A substrate may be formed of and/or include a coating formed of a hydrophobic material, such as polyethylene. In an embodiment, a substrate may be a mesh commercially available from ACS Industries, Inc. (Woonsocket, R.I.). For example, a Polymer Mist Eliminator DWG No. 04-15841-01, style 8PP, 74 inch outer diameter, 12 inch thick polymesh may be used. In certain embodiments, the material selected to form the substrate may not substantially degrade in the presence of the wastewater to be treated.

Figure 3A:
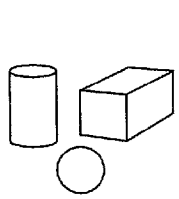
FIGS. 3A-C depict embodiments of substrates for a system for the reduction of contaminants in water.
Figure 3B:
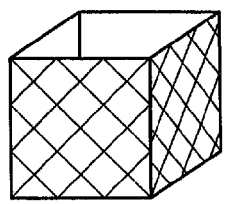
Figure 3C:
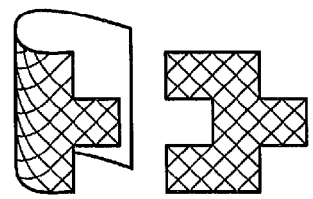

A substrate may be planar, substantially cylindrical, substantially conical, substantially spherical, substantially rectangular, substantially square, substantially oval shaped, and/or irregularly shaped. FIG. 3A depicts embodiments of different substrates. A substrate may have a shape similar to a cage, see FIG. 3B. A substrate may be knitted or woven mesh. A substrate may be corrugated and/or mesh. For example, a substrate may have a shape similar to an air filter. One or more substrates may be configured to couple to each other, see FIG. 3C.

In some embodiments, one or more bacteria may couple to a substrate in a container to form a biofilm. In an embodiment, bacteria forming the biofilm may not substantially slough off of the substrate, during use. The bacteria may be aerobic. Some of the bacteria may be oligotrophic, heterotrophic, enteric, and/or combinations thereof.

The bacteria may be capable of reducing contaminants in wastewater. In some embodiments, a biofilm may be capable of significantly reducing contaminants in water quickly. For example, wastewater may only have to reside in a container with the biofilm for less than 24 hours to significantly reduce an amount of contaminants in the wastewater.

One or more of the bacteria may reduce an amount of and/or degrade pesticides, industrial wastewater, wastewater from septic systems, and/or municipal wastewater. In some embodiments, one or more of the bacteria may reduce an amount of and/or degrade metal compounds and/or organic compounds such as alkanes, alkenes, aromatic organic compounds, and/or polychlorinated benzenes. Some bacteria may cleave long chain biopolymers into monomers, which other bacteria degrade. In an embodiment, bacteria may degrade at least a portion of organic compounds into at least carbon dioxide and water.

Figure 4A:
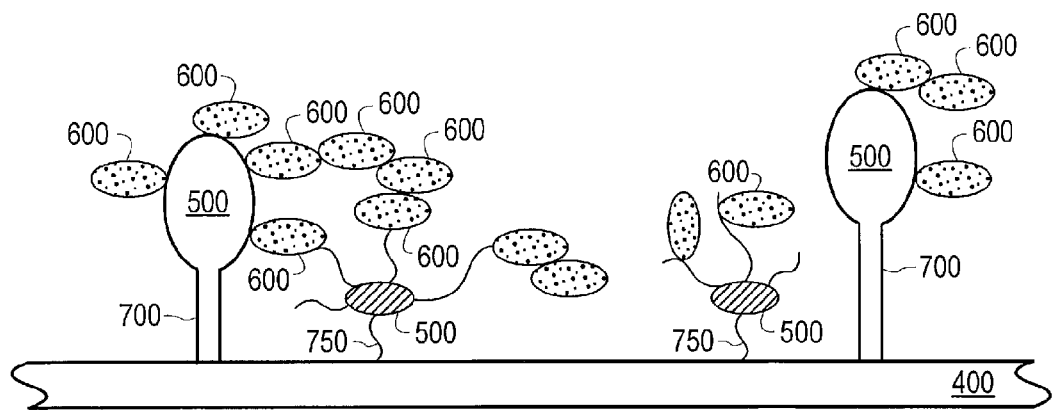
FIG. 4A depicts a representation of an embodiment of bacteria coupled to substrate.
Figure 4B:
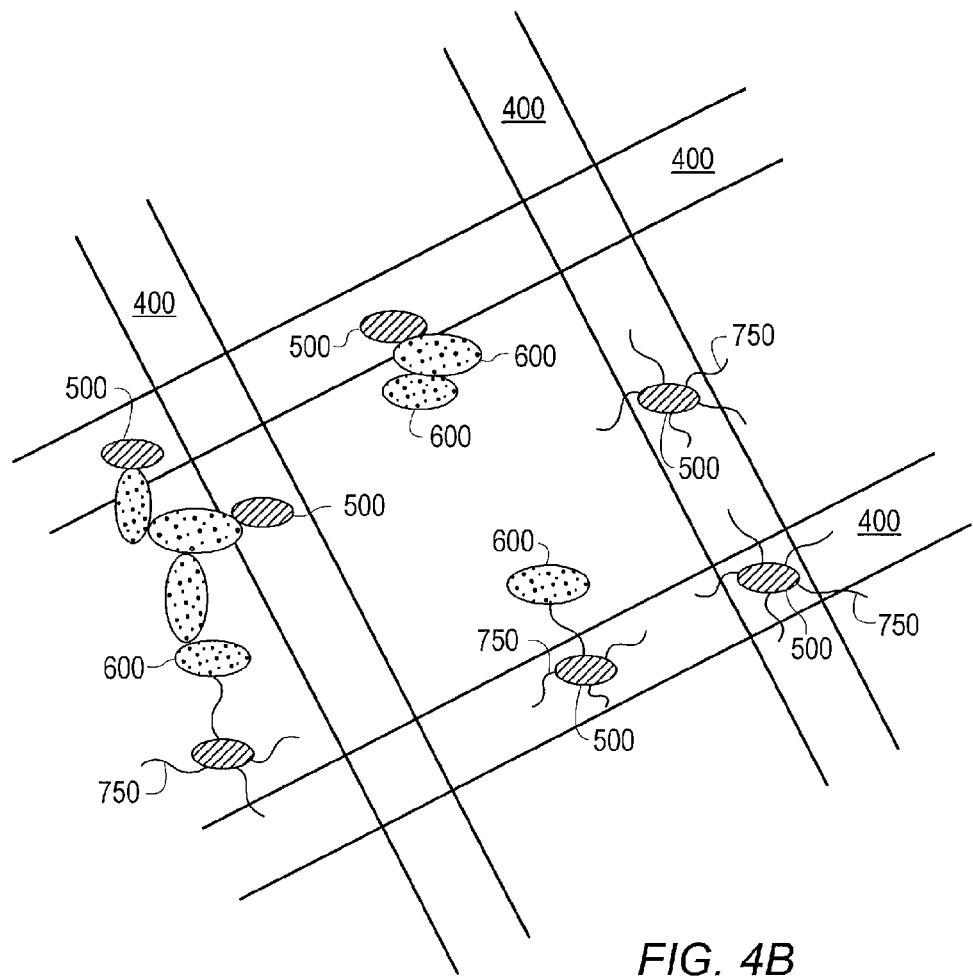
FIG. 4B depicts a representation of an embodiment of bacteria coupled to substrate.

In some embodiments, a biofilm may include one or more primary adherer bacteria 500 and/or one or more secondary adherer bacteria 600, see FIGS. 4A-4B. Primary adherer bacteria 500 may be capable of coupling to one or more substrates 400 in a container and/or other bacteria. In certain embodiments, primary adherer bacteria 500 may couple with a substrate 400 such that the primary adherer bacteria are inhibited from being dislodged from the substrate during use. In an embodiment, primary adherer bacteria 500 may irreversibly couple to a substrate 400.

Primary adherer bacteria may have longitudinal and latitudinal sides. In some bacteria, a longitudinal side may be longer than a latitudinal side or vice versa. Primary adherer bacteria may couple to bacteria and/or a substrate along a longitudinal and/or a latitudinal side. In an embodiment, a type of primary adherer bacteria may only couple to a substrate on one of its latitudinal sides. Another type of primary adherer bacteria may only couple to a substrate on one of its longitudinal sides. A shape and/or a density of a biofilm may be controlled by selecting one or more types of primary adherer bacteria that have a preference for coupling with substrate along a specific side.

In some embodiments, primary adherer bacteria 500 may include a stalk 700. For example, bacteria in the genus *Caulobacter* have a stalk. A stalk may be a narrower than the body of the primary adherer bacteria. A stalk may be capable of coupling to inanimate objects. An end of a stalk of a primary adherer bacteria maybe couple to an inanimate object, such as a substrate, but not couple to bacteria. For example, an end of a stalk of a primary adherer bacteria may include a holdfast, such as a sugar based holdfast, which allows the end of the stalk to bind with a substrate.

In an embodiment, a stalk may grow. A stalk of a primary adherer bacteria may be capable of growing from about 5 nm to about 200 nm. It may be advantageous to utilize a bacteria capable of extending a biofilm. If a food source is not plentiful proximate primary adherer bacteria with stalks, the stalks may grow to position the primary adherer bacteria in another region of the fluid with a greater food source.

Primary adherer bacteria 500 may include one or more filaments 750, such as organelle, capable of coupling with other bacteria. For example, bacteria in the genus *Gordonia* have several filaments. Some primary adherer bacteria may have filaments capable of coupling only with other types of bacteria (e.g., the filaments will not couple with the same primary adherer bacteria from the same genus).

In some embodiments, primary adherer bacteria may include bacteria from the class Actinobacteria Alphaproteobacteria, or combinations thereof. Primary adherer bacteria may include bacteria from the genus *Gordonia, Caulobacter*, or combinations thereof.

Secondary adherer bacteria 600 may be capable of coupling with one or more other bacteria including primary adherer bacteria 500. In some embodiments, secondary adherer bacteria 600 may not be capable of coupling to a substrate 400. In an embodiment, secondary adherer bacteria may include bacteria from the class Bacilli, Gammaproteobacteria, Betaproteobacteria, or combinations thereof. Secondary adherer bacteria may include bacteria from the genus *Bacillus, Pseudomonas, Zoogloea, Enterobacter*, or combinations thereof.

Primary adherer bacteria and/or secondary adherer bacteria may be capable of reducing contaminants in water. Secondary adherer bacteria may be capable of reducing a greater amount of one or more types of contaminants than one or more of the primary adherer bacteria. In some embodiments, sessile bacteria may experience gene-up regulation that increases the metabolic activity of the sessile bacteria. Sessile bacteria may have a metabolic activity 4 times the metabolic activity of planktonic bacteria. Primary adherer bacteria may experience gene-up regulation of metabolic activity due to their attachment to a substrate and/or secondary adherer bacteria may experience gene-up regulation due to their attachment to other bacteria. In an embodiment, sessile primary adherer bacteria may experience greater gene-up regulation of metabolic activity that sessile secondary adherer bacteria.

In some embodiments, bacteria provided to a container may be selected to reduce specific contaminants. Bacteria may be selected for their ability to withstand a pre-determined amount of a contaminant, such as 100 ppm of aromatic organic compound, and/or fluctuations in pH. For example, bacteria selected may include bacteria from the genus *Enterobacter, Pseudomonas, Gordonia, Bacillus, Agrobacterium, Caulobacter*, and/or *Zoogloea*. The biofilm may include bacteria in the genus *Nocardia, Thiothrix* or *Beggiatoa*. In an embodiment, a biofilm may include *Enterobacter cloacae, Pseudomonas putida, Pseudomonas stutzeri, Gordonia* sp., *Bacillus subtilis, Agrobacterium* sp., *Caulobacter vibrioides*, and/or bacteria in the genus *Zoogloea*. In another embodiment, a biofilm may be formed from a combination of bacteria, such as FreeFlow®, commercially available from NCH Corp (Irving, Tex.).

Figure 5A:
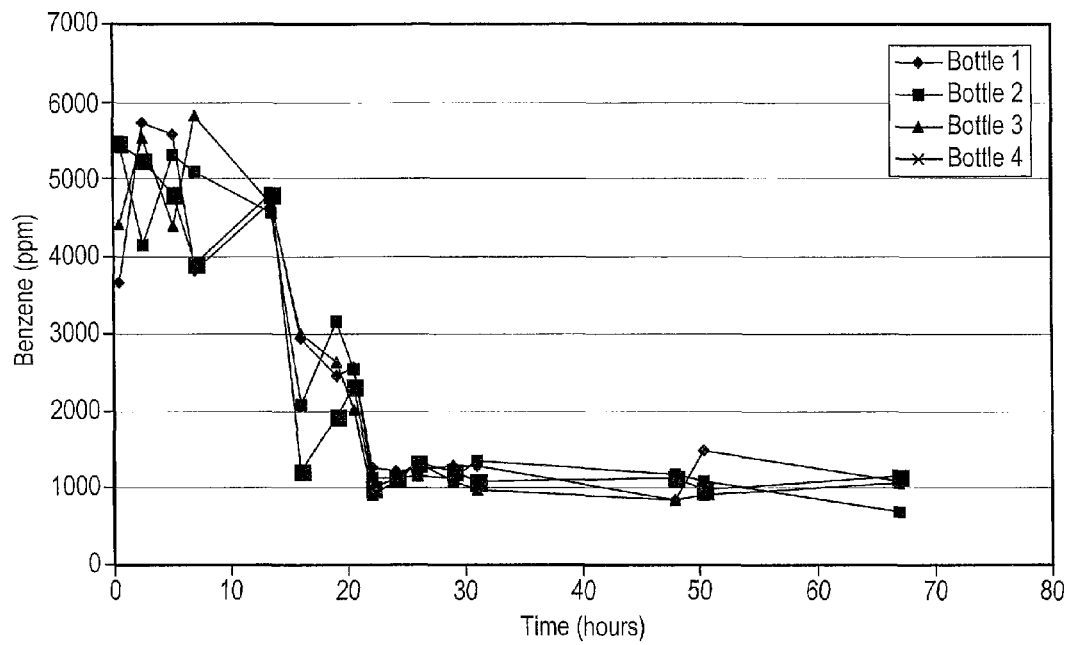
FIGS. 5A-B depict graphs that show the change in concentration of benzene over time in an embodiment of a system that includes bacteria in the genus *Gordonia*.
Figure 5B:
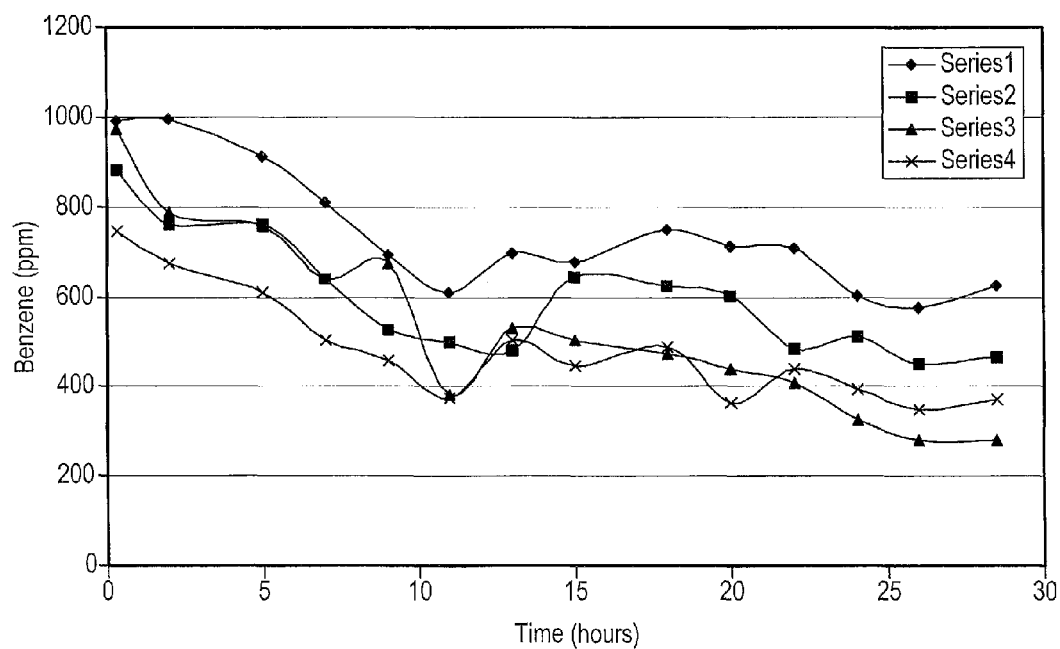
Figure 6:
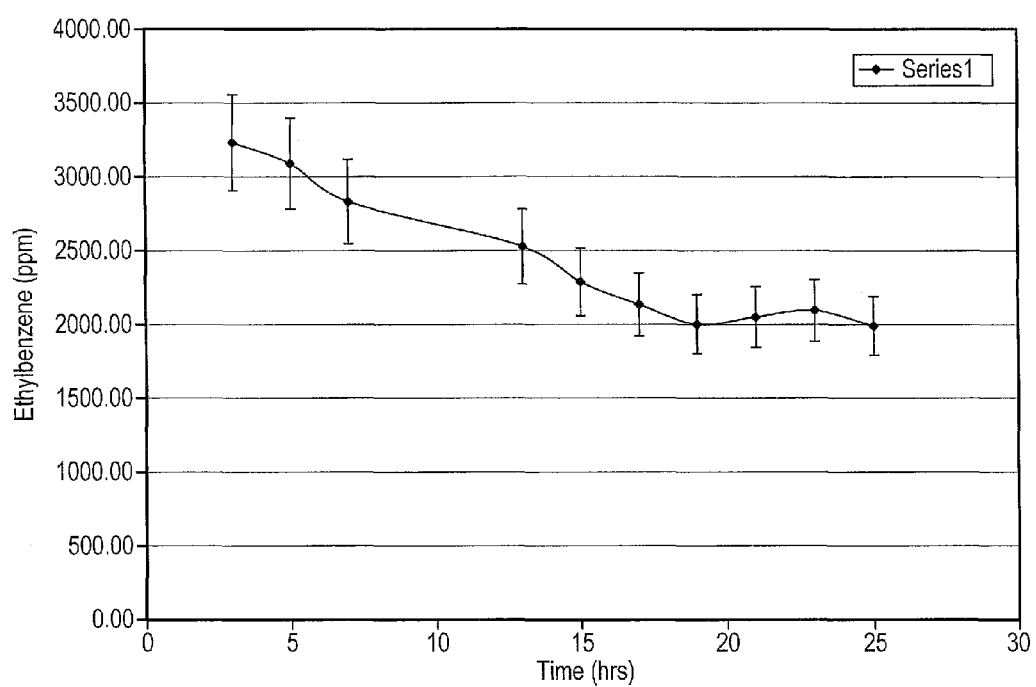
FIG. 6 depicts a graph that shows the change in concentration of ethylbenzene over time in an embodiment of a system that includes bacteria in the genus *Gordonia*.

In some embodiments, the biofilm may include bacteria of the phylum Actinobacteria phy. nov., class Actinobacteria, subclass Actinobacteridae, order Actinomycetales, suborder Corynebacterineae, family Gordoniaceae, and/or genus *Gordonia*. In some embodiments, bacteria in the genus *Gordonia* may have filaments. The filaments may be capable of binding with a substrate and/or other bacteria. The filaments may promote formation of a more even biofilm. Bacteria in the genus *Gordonia* may be capable of degrading one or more organic compounds, such as benzene, toluene, ethylbenzene, o-xylene, p-xylene, and/or m-xylene. A system including bacteria in the genus *Gordonia* coupled to a substrate may be capable of reducing an amount of benzene in wastewater, see. FIGS. 5A-B which depicts a graphical representation of the removal of benzene by the system. A system including bacteria in the genus *Gordonia* that is coupled to a substrate may reduce an amount of ethylbenzene in an aqueous solution, see FIG. 6 which depicts a graphical representation of the removal of ethylbenzene by a system.

In some embodiments, a biofilm including bacteria in the genus *Gordonia* may be capable of degrading rubber compounds, desulphurize aromatics, and/or degrade pyridine compounds. Bacteria in the genus *Gordonia* may be capable of removing sulfur from petrochemical products. In an embodiment, bacteria in the genus *Gordonia* may produce biosurfactants that facilitate remediation and/or degradation of organic and metal-based contamination. Biosurfactants may assist in the solubilization of various pollutants and/or allow bacteria to more rapidly uptake pollutants for degradation or immobilization.

Bacteria in the genus *Gordonia* may go into a state of latency during periods of stress, introduction of a toxin, nutrient deprivation, and/or oxygen deprivation. Bacteria in the genus *Gordonia* may be capable of reviving out of the state of latency once the environment becomes conducive to the bacteria. It may be advantageous to utilize bacteria capable of going into a latent state and reviving, so that bacteria in a biofilm may not die if the environment, such as in a bioreactor, changes significantly.

Figure 7A:
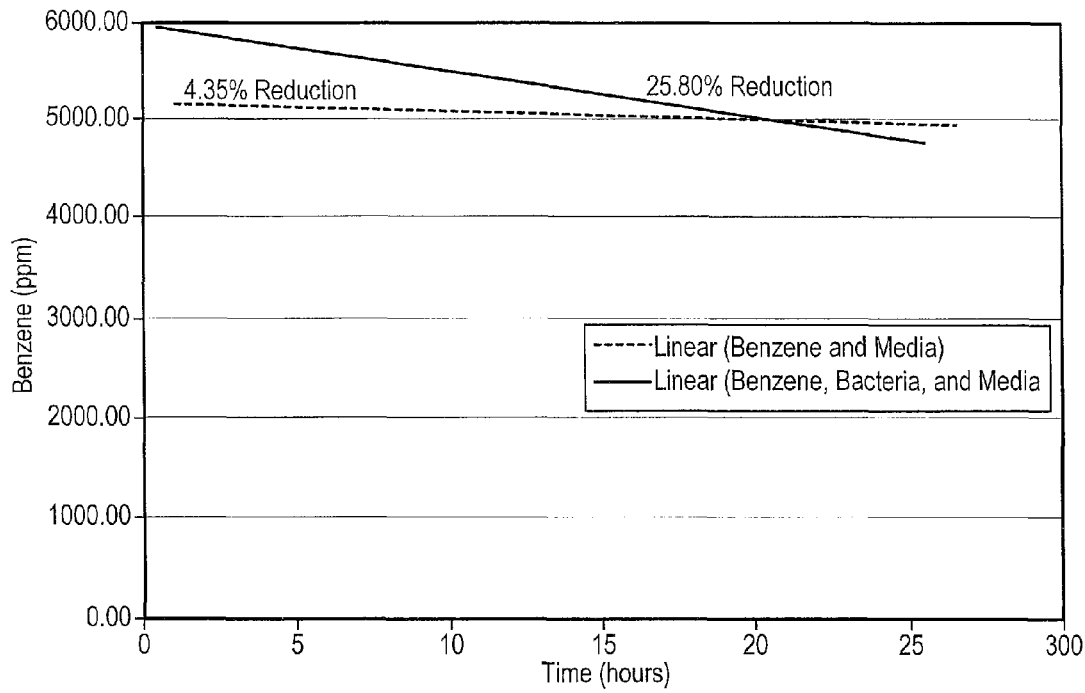
FIG. 7A depicts a graph that shows the change in concentration of benzene over time in an embodiment of a system that includes bacteria in the genus *Gordonia* but does not include substrate.
Figure 7B:
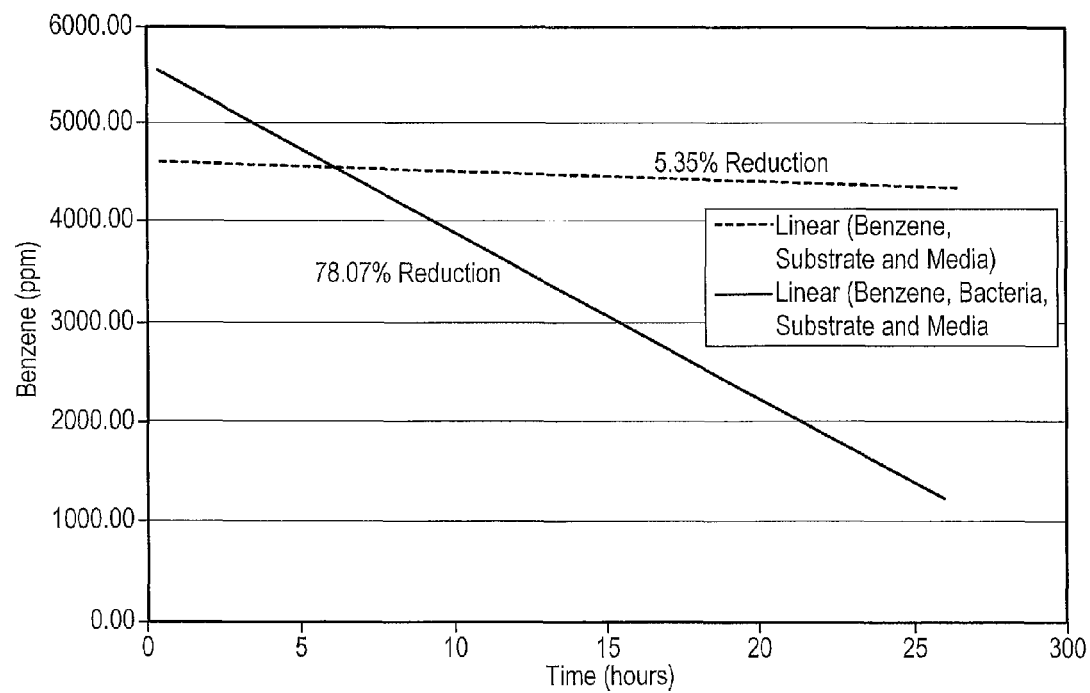
FIG. 7B depicts a graph that shows the change in concentration of benzene over time in an embodiment of a system that includes bacteria in the genus *Gordonia* coupled to a substrate.

Bacteria in the genus *Gordonia* may cause foaming in wastewater treatment systems. However, when bacteria in the genus *Gordonia* are coupled to a substrate, foaming is inhibited and gene-up regulation occurs causing the bacteria to be capable of reducing contaminants from water. FIG. 7A depicts a graph of benzene concentrations over time in a control system (e.g., without bacteria) and in an embodiment of a system that includes bacteria in the genus *Gordonia* but no substrate. FIG. 7B depicts a graph of benzene concentrations over time in embodiments of a system that includes substrate and bacteria in the genus *Gordonia* and a system that includes a substrate and without bacteria. As shown in the graphs, bacteria in the genus *Gordonia* is capable of degrading more benzene when coupled to a substrate that when the bacteria is not coupled to substrate. The phenomena of bacteria possessing a greater ability to degrade and/or reduce contaminants more efficiently when bound (e.g., gene-up regulation) is not limited to bacteria in the genus *Gordonia* but is present in several types of bacteria. Using bacteria with increased contamination reduction abilities when bound allows formation of a more stabile biofilm (e.g., since bacteria are coupled to the substrate) and/or a more efficient biofilm.

In some embodiments, the biofilm may include bacteria of the phylum Proteobacteria phy. nov., class Alphaproteobacteria, order Caulobacterales, family Caulobacteraceae, and/or genus *Caulobacter*. Bacteria in the genus *Caulobacter* may convert heavy metals such as mercury, copper, cadmium, and cobalt in aqueous solutions into chemical forms that are less toxic, less soluble, and/or precipitate out of solution. Some bacteria in the genus *Caulobacter* have resistance to some antibiotics such as chloramphenicol, tetracycline, erythromycin, and tobomycin. Resistant bacteria may be from plasmid transfer between antibiotic resistant intestinal or human associated bacteria found in wastewater and bacteria in the genus *Caulobacter*.

Bacteria in the genus *Caulobacter* are oligotrophs and may be capable of surviving in low carbon concentration environments. In some embodiments, bacteria in the genus *Caulobacter* may be capable of forming a uniform biofilm due to the bacteria shape. Bacteria in the genus *Caulobacter* have a motile stage characterized by a swarmer cell and a sessile stage characterized by a stalk shaped cell. The stalks of the bacteria in the genus *Caulobacter* may grow. It may be desirable to use a bacteria with a growing stalk since the bacteria may be better able to survive changes in environment. For example, if nutrients proximate a bacterium's location are depleting, then the stalk of the bacterium in the genus *Caulobacter* may grow and the bacterium can be positioned in a new location with a more nutrients.

While some bacteria are capable of forming a biofilm through the secretion of polysaccharides, bacteria in the genus *Caulobacter* may be capable of forming a biofilm using a stalk. In an embodiment, using bacteria with stalks may allow the creation of a more uniform biofilm when compared with a biofilm formed without the use of bacteria with filaments. For example, a biofilm may be formed of a first layer including bacteria in the genus *Caulobacter* and one or more other layers coupled to the bacteria in the genus *Caulobacter*. The stalks may be capable of coupling to the substrate but may not be capable of coupling to other bacteria. In an embodiment, bacteria in the genus *Caulobacter* may only couple with a substrate at the holdfast at an end of its stalk.

In an embodiment, bacteria in the genus *Caulobacter* are capable of frequently entering and exiting a stationary phase. It may be desirable to utilize bacteria capable of entering and exiting the stationary phase, because the bacteria may be more durable and/or capable of surviving environments with fluctuations in levels of nutrients.

In some embodiments, the biofilm may include bacteria of the phylum Proteobacteria phy. nov., class Gammaproteobacteria, order Enterobacteriales, family Enterobacteriaceae, and/or genus *Enterobacter*. Bacteria in the genus *Enterobacter* may be enteric, anerobic, and a heterotroph. Bacteria in the genus *Enterobacter* may produce hydrogen when metabolizing organic compounds. Bacteria in the genus *Enterobacter* may be capable of degrading aromatics, such as 2,4,6-trinitrotoluene that is commonly found in wastewater produced in munitions production. Bacteria in the genus *Enterobacter* may be capable of degrading nitrate esters, such as pentaerythritol tetranitrate and glycerol trinitrate.

In some embodiments, the biofilm may include bacteria of the phylum Firmicutes phy. nov., class Bacilli, order Bacillales, family Bacillaceae, and/or genus *Bacillus*. Bacteria in the genus *Bacillus* may be good oligotrophs and capable of surviving in an environment with a low concentration of organic compounds. Bacteria in the genus *Bacillus* may be capable of degrading organic compounds, such as organic compounds produced from plant and animal sources (e.g., cellulose, starch, pectin, proteins, hydrocarbons). In an embodiment, a biofilm comprising bacteria in the genus *Bacillus* may cleave long chain biopolymers into monomers that are degradable by other bacteria. Bacteria in the genus *Bacillus* may be cable of nitrification, denitrification, and/or nitrogen fixation. Bacteria in the genus *Bacillus* may be capable of fermenting carbohydrates, producing glycerol and butanediol, producing enzymes for utilization in detergents, paralyzing insects, degrading biopolymers, and/or synthesis for use in industrial processes such as the production of antibiotics.

In some embodiments, it may be desirable to utilize bacteria in the genus *Bacillus* to create a biofilm capable of surviving in harsh environments. Bacteria in the genus *Bacillus* may produce spores that are highly resistant to stressful environments and/or toxic environments. Bacteria in the genus *Bacillus* may synthesize antibiotics that kill proximate bacteria and cause the dead bacteria to lyse and release their contents. Bacteria in the genus *Bacillus* may absorb the nutrients released by the ruptured cells. This process may require less energy than forming spores.

In some embodiments, the biofilm may include bacteria of the phylum Proteobacteria phy. nov., class Gammaproteobacteria, order Pseudomonadales, family Pseudomonadaceae, and/or genus *Pseudomonas*. Bacteria in the genus *Pseudomonas* may be good heterotrophs. Bacteria in the genus *Pseudomonas* may be capable of degrading organic compounds, such as trichloroethylene. In an embodiment, bacteria in the genus *Pseudomonas* may degrade monomer organic compounds. Bacteria in the genus *Pseudomonas* may be capable of degrading aromatic organic compounds such as toluene, xylene, naphthalene, or polynuclear aromatic organic compounds. In certain embodiments, bacteria in the genus *Pseudomonas* may prefer to degrade simple organic compounds when compared to other organisms.

In some embodiments, it may be desirable to include bacteria in the genus *Pseudomonas* in a biofilm since they are capable of withstanding fluctuations in environment. Bacteria in the genus *Pseudomonas* may produce o-acetylated alginate that encapsulates the bacteria to protect the bacteria from stressful environments. Bacteria in the genus *Pseudomonas* may have filaments. The filaments may help bacteria in the genus *Pseudomonas* to attach to substrates and/or other organisms. The filaments and production of alginate by bacteria in the genus *Pseudomonas* may promote formation of a biofilm and/or formation of a biofilm coupled to a substrate.

In certain embodiments, the biofilm may include bacteria of the phylum Proteobacteria phy. nov., class Betaproteobacteria, order Rhodocyclales, family Rhodocyclaceae, and/or genus *Zoogloea*. Bacteria in the genus *Zoogloea* may be a good heterotroph. Bacteria in the genus *Zoogloea* may be capable of degrading high concentrations of proteins. Bacteria in the genus *Zoogloea* may produce exopolysaccharide that contributes to the ability of a biofilm containing bacteria in the genus *Zoogloea* to tolerate fluctuating, stressful, and/or toxic environments.

In various embodiments, the biofilm may include bacteria of the phylum Actinobacteria phy. nov., class Actinobacteria, order Actinomycetales, suborder Corynebacterineae, family Nocardiaceae, and/or genus *Norcardia*; bacteria of the phylum Proteobacteria phy. nov., class Gamma proteobacteria, order Thiotrichales, family Thiotrichaceae, and/or genus *Thiothrix*; and/or bacteria of the phylum Proteobacteria phy. nov., class Gamma proteobacteria, order Thiotrichales, family Thiotrichaceae, and/or genus *Beggiatoa*. Bacteria of the suborder Corynebacterineae and bacteria of the family Thiotrichaceae may have similar behavior. For example, both may experience gene-up regulation of metabolic activity when attached to a substrate. In an embodiment bacteria of the suborder Corynebacterineae and bacteria of the family Thiotrichaceae may cause foaming in a container when planktonic.

Bacteria in the genus *Gordonia* may be capable of degrading one or more organic compounds, such as benzene, toluene, ethylbenzene, o-xylene, p-xylene, and/or m-xylene. A system including bacteria in the genus *Gordonia* coupled to a substrate may be capable of reducing an amount of benzene in wastewater, see. FIGS. 5A-B which depicts a graphical representation of the removal of benzene by the system. A system including bacteria in the genus *Gordonia* that is coupled to a substrate may reduce an amount of ethylbenzene in an aqueous solution, see FIG. 6 which depicts a graphical representation of the removal of ethylbenzene by a system.

In some embodiments, one or more bacteria generators may provide one or more of the bacteria that form, supplement, and/or replenish the biofilm in a container. Bacteria generator may be a container capable of incubating one or more types of bacteria. In an embodiment, bacteria generator may produce more than one type of bacteria simultaneously. In another embodiment, a system may include bacteria generator for each strain or set of strains of bacteria that form the biofilm. Bacteria generator may be a BioAmp®, commercially available from NCH Corp (Irving, Tex.). Bacteria generator may include one or more nutrient sources and/or be coupled to one or more containers such that bacteria from the bacteria generator is provided to the container. Bacteria generator may be capable of producing a predetermined amount of bacteria in less than 48 hours. In an embodiment, bacteria generator may be capable of producing a predetermined amount of bacteria in less than 24 hours.

Bacteria generator may be capable of producing a constant supply of bacteria to a container. In certain embodiments, bacteria generator may incubate bacteria as described in U.S. Pat. No. 5,599,451 to Guiot, which is incorporated by reference. In an embodiment, bacteria generator may facilitate rapid formation of a biofilm in a container, since bacteria can be supplied to the biofilm to supplement growth of the bacteria in the container. Bacteria generator may be capable of producing different combinations and/or ratios of bacteria during use. In addition, unlike many automated bacteria incubators, the bacteria generator may be capable of inoculating the bacteria in the bacteria generator, as desired.

In some embodiments, one or more air sources may be coupled to one or more containers and/or one or more bacteria generators to provide air or oxygen. An air source may be positioned on a top surface of a container. An air source may provide Vacuum Bubble Technology (VBT) aeration, such an air source commercially available from Advanced Aeration, Inc (Angleton, Tex.). An air source may substantially maintain an aerobic environment in the container and/or the bacteria generator.

In certain embodiments, an air source may produce an air bubble stream. An air source may be configured to produce bubbles with a fixed or variable air bubble diameter. An air source may produce air bubbles with an average bubble diameter less than approximately 1 mm. In an embodiment, an air source may produce air bubbles with an average bubble diameter less than approximately 5 mm. An air source may produce air bubbles with an average bubble diameter from approximately 0.5 mm to approximately 0.2 mm. In another embodiment, an air source may produce air bubbles with an average bubble diameter from approximately 0.3 mm to approximately 0.2 mm.

An air source may produce bubbles with a buoyancy less than the surface tension of water and/or wastewater in a container. An air source may produce bubbles capable of remaining diffused in fluids in a container for approximately 6 to 12 hours rather than floating to a top surface of the fluid. In an embodiment, an air source may produce air bubbles in at least a partial vacuum. In certain embodiments, an air source may produce bubbles filled with gas or combinations of gasses, such as oxygen, nitrogen or carbon dioxide.

In some embodiments, the air source may assist in fluid mixing in a container. An air bubble stream may flow from the air source with a force sufficient to at least partially mix fluids in a container. In an embodiment, an air source may produce turbulent areas that agitate fluids in the container and/or increase contact between the bacteria and the contaminants to allow faster reduction in the amount of contaminants. An air source may be coupled proximate a stirrer in a container to amplify the mixing provided by a stirrer in a container.

An air source that provides an air bubble stream may be preferable to a forced air diffuser, air compressor, and surface aerators that pump air into a water column. Pumping air into a water column may form large bubbles which quickly float out of the water column. Water can only contain 8 molecules of oxygen per million molecules of water, therefore when large bubbles of air are produced and quickly travel through a water column, the probability that oxygen will diffuses into the water is low. Thus, using small bubbles, and as a result increasing the total surface area of air bubbles exposed to water, increases the probability that oxygen will diffuse into the water. In addition, using bubbles that remain in fluid in the container for at least 6 hours increases the exposure time of the bubbles to the fluid and thus increases the probability of oxygen diffusion into the fluid.

In some embodiments, a system for reduction of contaminants may include a controller. A controller may be configured to automate the system. The controller may measure various parameters of the system, such as pressure; temperature; pH; amount of contaminants in a container, a wastewater stream, and/or an outlet stream; an amount, type, and/or ratio of types of bacteria in a container; an amount of bacteria that settles at a bottom of a container; an amount of solids collected at a bottom of a container; flow rates of wastewater, streams of bacteria from bacteria generator, air bubble stream, and/or drains; and/or a volume of water in a container and/or bacteria generator. A controller may use measurements of the various parameters to modify values of one or more parameters of the system, such as flow rates of bacteria, wastewater stream, and/or outlet stream; temperatures; pH; and/or average diameters of air bubbles produced in an air source. A controller may measure and/or modify parameters of the system continuously or periodically.

In an embodiment, a controller may determine an amount of bacteria and/or types of bacteria in a container and alter a flow rate of bacteria from bacteria generator into the container and/or types of bacteria produced in bacteria generator. In another embodiment, a controller may detect a biological oxygen demand (BOD) level and modify a flow rate of wastewater, nutrients, and/or air bubble stream into the container. A controller may detect a level of contaminants in the container and allow at least a portion of the fluid in the container to flow from the container.

In some embodiments, the system may include one or more platforms. A platform may be movable. A platform may facilitate the transportation of the system. A platform may have wheels and/or be movable with a forklift.

A platform may be formed of metal, wood, fiberglass, plastic, and/or a combination thereof. A platform may have a top surface that is substantially circular, substantially elliptical, substantially oval, substantially square, substantially rectangular, or irregularly shaped. In an embodiment, the top surface and the bottom surface of a platform may have a similar shape and/or size.

In certain embodiments, the platform may be selected to meet shipping and/or transportation requirements. A platform may be a 463L pallet to comply with shipping requirements on a plane, such as a C-130.

It may be advantageous to utilize a system comprising platforms to create a mobile remediation system. In some embodiments, the system may include one or more containers, bacteria generators, and/or air sources positioned in or on one or more platforms. The system may be transported on more than one platform and be positioned at a desired location. Once the system is at the desired location, the components of the system (e.g., containers, bacteria generators, air sources, and/or controllers) may be coupled. In certain embodiments, more than one component may be on a platform. For example, an air source may be positioned on top of a container positioned in or on a platform.

Figure 8:
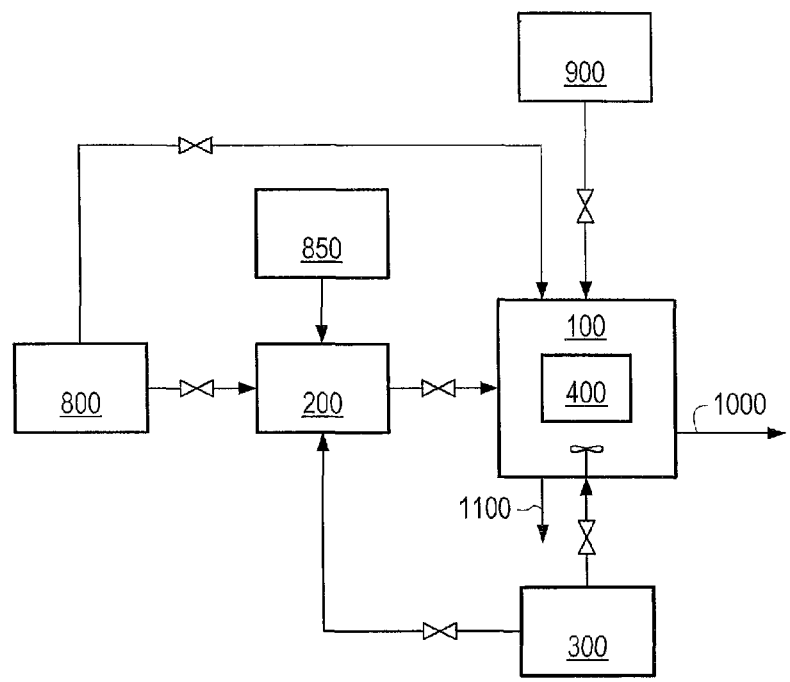
FIG. 8 depicts an embodiment of a system for the reduction of contaminants in water.
Figure 9:
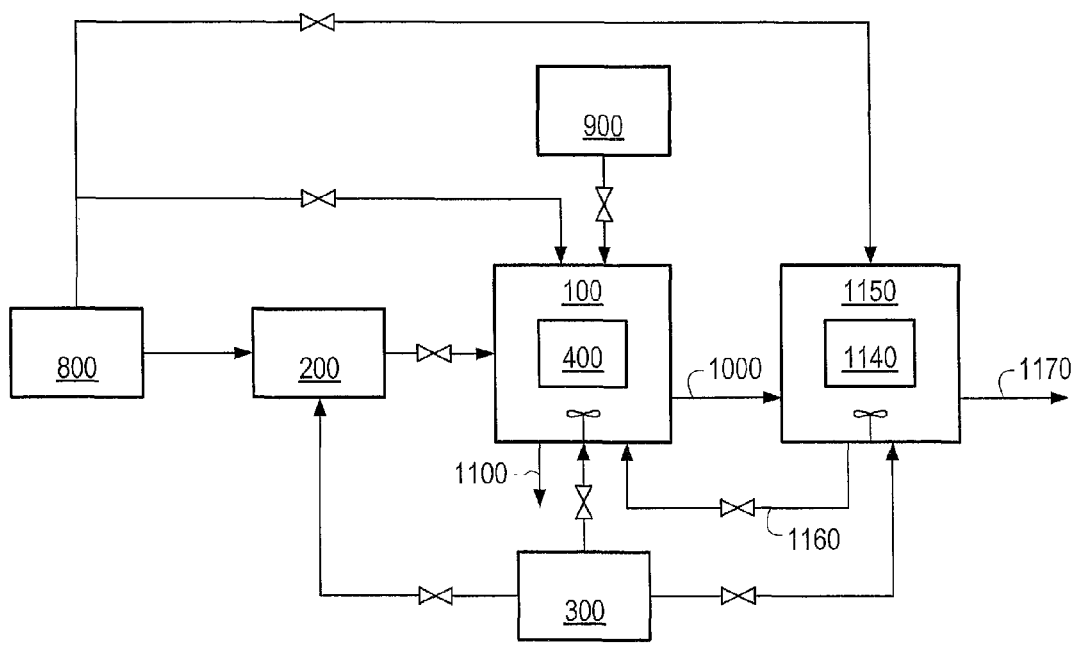
FIG. 9 depicts an embodiment of a system for the reduction of contaminants in water in which fluid is recycled through multiple containers.

FIGS. 8-9 depict embodiments of systems for the reduction of contaminants. One or more types of bacteria 850 may be added to bacteria generator 200. Nutrients 800 may be added to the bacteria generator 200. An air stream may be provided to the bacteria generator 200 from one or more air sources 300. Bacteria in the bacteria generator 200 may incubate and/or reproduce to generate a desired quantity and/or ratio of bacteria. In an embodiment, a predetermined quantity of bacteria sufficient to promote production of a biofilm in a container may be produced in less than 48 hours.

Once a predetermined amount of bacteria is produced in the bacteria generator 200, bacteria from the bacteria generator may be introduced into the container 100. One or more nutrients 800 may be delivered to the container 100 to promote the formation of a biofilm in the container. An air bubble stream may be provided to the container 100 from one or more air sources 300 coupled to the container. A biofilm may be allowed to form on the substrate 400 in the container 100. In some embodiments, a biofilm may be formed in a container prior to introduction of wastewater. In another embodiment, a biofilm may be formed in the presence of wastewater in a container.

Figure 10:
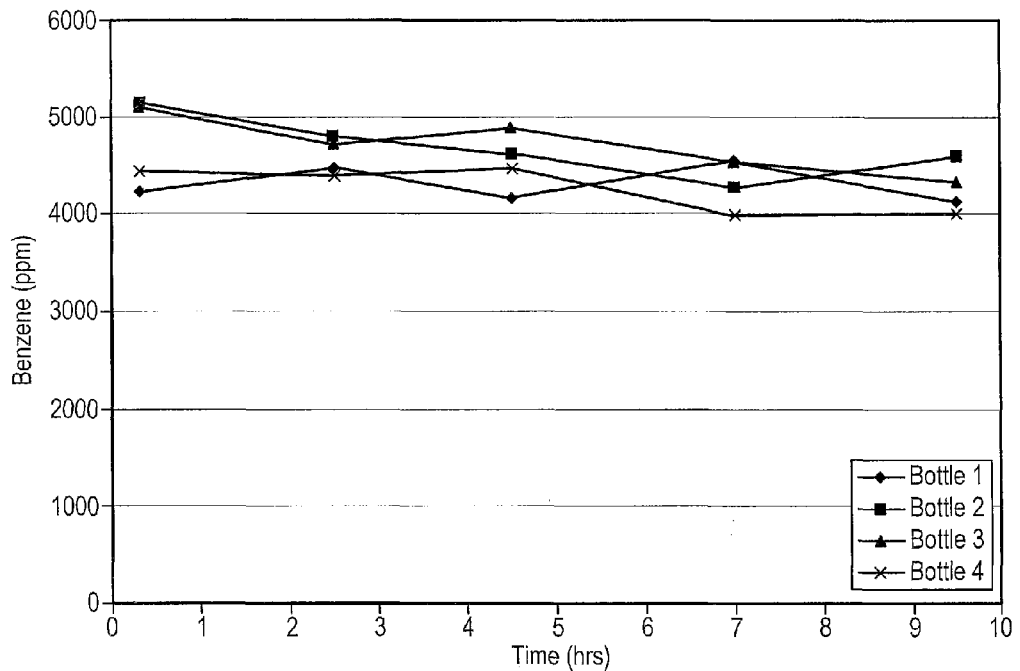
FIG. 10 depicts a graph that shows the change in concentration of benzene over time in an embodiment of a system in which nutrients are not added to the system.

After at least a portion of the biofilm is formed in the container 100, wastewater 900 may be introduced into the container. The biofilm may reduce the amount of contaminants in the wastewater. The bacteria of the biofilm may absorb, immobilize, entrap, degrade, consume, and/or modify the contaminants in the wastewater. Nutrients 800 may be added to the container 100, if the wastewater does not contain sufficient nutrients for the biofilm, such as when degrading volatile organic compounds. For example, a system that includes bacteria in the genus *Gordonia* coupled to a substrate may need a minimal level of nutrients (e.g., glucose or other contaminants in the wastewater) to degrade benzene, as depicted in FIG. 10 which shows a low reduction in benzene in solutions that lack other nutrients.

When the level of contaminants in the wastewater has been reduced to or below an allowable level of contamination, fluid 1000 may flow from the container 100, see FIGS. 8-9. The fluid 1000 may flow from the container 100 after residing in the container for less than approximately 20 hours or less than approximately 8 hours. In an embodiment, one or more additional containers 1150 with a biofilm 1140 may process fluid 1000 flowing from the container 100, as depicted in FIG. 9. Fluid flowing from the additional container 1150 may be recycled 1160 through a container 100 and/or flow from an outlet 1170 in the additional container with less contaminants than the wastewater 900. In an embodiment, industry standards, treaties, the United States Environmental Protection Agency, and/or other regulatory agency may determine an allowable level of contamination in the fluid. In an embodiment, wastewater may be continuously delivered to the container 100 and fluids 1000 may continuously flow out of the container with less contaminants than the wastewater.

In some embodiments, it may be necessary to replenish and/or replace at least a portion of the bacteria that form the biofilm. The controller may detect a level of bacteria in the container and allow an amount of bacteria to flow into the container from one or more bacteria generators. In response to measured bacteria levels in the container, the controller may modify an amount of bacteria that flows from the bacteria generator to the container and/or amounts of bacteria, nutrients, and/or air delivered to the bacteria generator and/or the container.

In an embodiment, a biofilm may be replaced in response to substantially decreased level of bacteria in the container and/or a substantially decreased level of reduction of contaminants detected by the controller. In addition, since some bacteria couple strongly with substrates even when dead, a substrate for a biofilm may be replaced and/or cleaned prior to forming a new biofilm in the container. A biofilm may be replaced by removing at least a portion of a substrate and then replacing the removed substrate with a new or a cleaned substrate.

In an embodiment, solids in the wastewater 900 may sink to the bottom of the container 100. Bacteria may separate from the biofilm and/or die and uncouple from the biofilm and sink to the bottom of the container 100. A drain 1100 in the container 100 may allow solids to be removed from the bottom of the container, during use.

During use, some systems for the reduction of contaminants and/or wastewater treatment plants may have foaming. Foaming may cause problems in continuous operation of a wastewater treatment plant by inhibiting contact between contaminants in the wastewater and the biofilm, altering mixing properties of a container, and/or blocking inlets and/or outlets. Some bacteria, such as bacteria in the genus *Gordonia, Nocardia, Microthrix*, and/or bacteria in the family Thiotrichaceae, such as bacteria in the genus *Thiothrix* and *Beggiatoa*, may cause foaming in wastewater treatment systems. In some embodiments, one or more hydrophobic substrates may be added to a container in a wastewater treatment plant that has foaming. The bacteria at least partially causing the foaming may couple to the hydrophobic substrates and foaming may be reduced and/or inhibited. When the bacteria, such as bacteria in the genus *Gordonia, Nocardia, Microthrix*, and/or bacteria in the family Thiotrichaceae, such as bacteria in the genus *Thiothrix* and *Beggiatoa*, couples to the hydrophobic substrate, gene-up regulation occurs and the bacteria is capable of reducing contaminants in water. Several other types of bacteria exhibit similar gene-up regulation behavior to bacteria in the genus *Gordonia*. In an embodiment, the bacteria, such as bacteria in the genus *Gordonia, Nocardia, Microthrix*, and/or bacteria in the family Thiotrichaceae, such as bacteria in the genus *Thiothrix* and *Beggiatoa*, may couple to the substrate rather than the container because the hydrophobic substrate has less electrostatic interference than the container. In some embodiments, the addition of a hydrophobic substrate to a wastewater treatment system with foaming may substantially eliminate foaming in the wastewater treatment system.

In some embodiments, a controller may monitor foaming in a wastewater treatment plant. When foaming reaches a predetermined level, the controller may allow substrates to be added to the container with foaming. In certain embodiments, the controller may automatically allow substrates to be added to the container with foaming that exceeds a predetermined level. In an embodiment, the controller may produce a signal indicating that foaming has reached a predetermined level and/or indicate to an operator that substrates should be added to the container with foaming.

It may be desirable to preserve bacteria for later use. In some embodiments, bacteria generator may be used to preserve bacteria. Preserved bacteria may be stored for as long as approximately one year without substantially affecting the bacteria's capability to return to a growth phase. In an embodiment, preserved bacteria may be stored for approximately six months without substantially affecting the bacteria's capability to return to a growth phase. Preserved bacteria may be used for a variety of purposes including in systems for the reduction of contaminants in wastewater. In an embodiment, preserved bacteria may be supplied to bacteria generator to produce a desired amount of bacteria to create and/or to supplement a biofilm.

Figure 11:
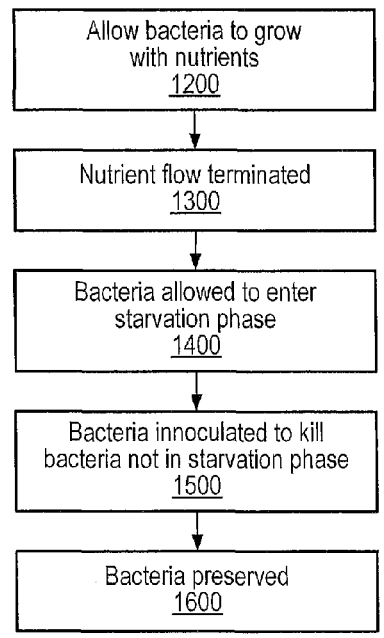
FIG. 11 depicts a flowchart of an embodiment of a method of preserving bacteria.

FIG. 11 depicts a flowchart of an embodiment of preserving bacteria. One or more types of bacteria are incubated and allowed to grow and/or reproduce in the presence of one or more nutrients 1200. In an embodiment, bacteria may be incubated and reproduce in one or more bacteria generators. The flow of nutrients is then terminated 1300 and the bacteria are allowed to enter a starvation phase 1400. In an embodiment, the starvation phase for the bacteria may be identified by determining when exponential growth of the bacteria has ended. The change in the number of bacteria may be monitored spectroscopically. The bacteria in the starvation phase may then be preserved 1600.

In some embodiments, the bacteria may be inoculated prior to preservation. Bacteria in the starvation phase produce stress proteins that protect the bacteria from shock. Therefore, when bacteria are inoculated, a greater percentage of bacteria in the starvation phase would be able to survive the shock due to the increased production of stress proteins. Stressing bacteria prior to preservation may allow hardier bacteria to survive the stress of inoculation while the weaker bacteria may die during inoculation. Therefore, it may be advantageous to stress bacteria prior to preserving the bacteria, since the shock may only allow hardier bacteria to be preserved.

It may be advantageous, in some embodiments, to preserve bacteria in the starvation phase. The starvation phase occurs during the stationary phase of bacteria. During the starvation or stationary phase, the rate of change of the number of bacteria is approximately constant since the number of bacteria generated is approximately the same number of bacteria that die. Using bacteria in the starvation phase may also be desirable, since when starved bacteria are introduced into an environment with nutrients, the bacteria are hungrier and more competitive for the available carbonaceous material.

In some embodiments, bacteria in the starvation phase may be preserved as bacteria-alginate beads, where the bacteria is immobilized in a bead. To produce bacteria-alginate beads, bacteria is mixed with an alginate, such as sodium alginate. In an embodiment, alginate is added to an aqueous solution including the bacteria in the starvation phase. In another embodiment, bacteria in the starvation phase may be added to an aqueous alginate solution. The sodium alginate or a viscous aqueous solution containing alginate may be autoclaved at a temperature from approximately 115° C. to approximately 125° C. The bacteria-alginate mixture is stirred. The viscosity of the bacteria-alginate mixture may increase while stirring. The bacteria-alginate mixture is then added to an aqueous solution containing calcium ions.

In an embodiment, the bacteria-alginate mixture is added in drops to the aqueous solution containing calcium ions. Bacteria-alginate particles are allowed to form in the calcium ion solution. The bacteria-alginate particles may be firm and not as compressible as a gelatinous substance. The bacteria-alginate particles may be separated from the solution and/or dried. The bacteria-alginate particles may be filtered from the solution in an aseptic environment. The preserved bacteria-alginate particles may be stored until needed and/or used in bacteria generator in a system for the reduction of contaminants in water. In an embodiment, when the bacteria-alginate particles are revived in a solution of nutrients, the bacteria may consume and/or degrade the alginate portions of the particle.

The size and shape of the bacteria-alginate particles may be controllable. The amount of bacteria-alginate mixture added or dropped into the calcium solution may control the size of the particles formed. The bacteria-alginate mixture may be sprayed onto the aqueous solution containing calcium ions to produce small substantially spherical-shaped particles. Particles that are substantially cubic, pyramidal, conical, or irregularly shaped may also be formed.

In other embodiments, bacteria in the starvation phase may be preserved on hydrophobic substrates. To produce immobilized bacteria in the starvation phase on a hydrophobic substrate, bacteria may incubate in a solution containing one or more hydrophobic substrates until the bacteria are in the starvation phase. Alginate is mixed in an aqueous solution and may be autoclaved at a temperature from approximately 115° C. to approximately 125° C. The hydrophobic substrate that includes the bacteria in the starvation phase may then be introduced into the alginate solution. Alginate may at least partially saturate the hydrophobic substrate. The hydrophobic substrate then may be contacted with an aqueous solution containing calcium ions. The hydrophobic substrate may be separated from the solution and/or vacuum filtered. The hydrophobic substrate may be allowed to dry. In certain embodiments, the hydrophobic substrate containing preserved bacteria in the starvation phase may be stored until needed, used in bacteria generator in a system for reduction of contaminants in water, and/or added to a container to form a biofilm.

Although adding bacteria-alginate mixture to calcium ions is described, other metal ions solutions may be used successfully as well, including barium, copper, or zinc metal ion solutions. It may be desirable to use a calcium ion solution because calcium is available at a low cost from sources such as limestone and/or calcium is not generally considered a contaminant, unlike copper or zinc.

Preserving bacteria in particles or immobilizing bacteria on hydrophobic substrates may allow the preserved bacteria to be more resilient to environmental stress and/or toxins and/or may reduce cell mortality upon revival. Unlike when using preservation methods currently known in the art, such during lyophilization or the formation of compressed tablets, the bacteria are not dried to desiccation when bacteria are in particles or immobilized on substrates. Although lyophilized bacteria and compressed pellet bacteria have long shelf lives, it may take a long period for the bacteria to acclimate to surroundings and return to an exponential growth stage. Bacteria in particles and immobilized on substrates may become physiologically active within a shorter period of time since the cells do not have to be hydrated since they were not desiccated to the same extent during preservation.

In some embodiments, the preserved bacteria in particles and/or hydrophobic substrate may be added to bacteria generator to produce bacteria for a container in a system for the reduction of contaminants in wastewater. The preserved bacteria may be revived from the starvation phase and enter exponential growth phase when introduced into an aqueous solution containing nutrients. The preserved bacteria may consume the alginate in the particle and/or hydrophobic substrate. After a period of incubation, the bacteria may then be introduced into a container to form and/or replenish a biofilm. In an alternative embodiment, preserved bacteria in or on hydrophobic substrate may be added directly to a container to form a biofilm.

It is to be understood the invention is not limited to particular systems or biological species described which may, of course, vary. It is also to be understood that the terminology used herein is for the purpose of describing particular embodiments only, and is not intended to be limiting. As used in this specification, the singular forms "a", "an" and "the" include plural referents unless the content clearly indicates otherwise. Thus, for example, reference to "a substrate" includes a combination of two or more substrates and reference to "a primary adherer bacteria" includes mixtures of primary adherer bacteria.

Certain U.S. patents have been incorporated by reference. The text of such U.S. patents is, however, only incorporated by reference to the extent that no conflict exists between such text and the other statements and drawings set forth herein. In the event of such conflict, then any such conflicting text in such incorporated by reference U.S. patents is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

EXAMPLES

Example 1

Producing Bacteria in the Starvation Phase

Bacteria was incubated in a nutrient broth at a temperature of from approximately 25° C. to approximately 30° C. depending on which bacteria is being preserved. Bacteria in the genus *Agrobacterium, Bacillus, Caulobacter, Enterobacter, Gordonia, Zoogloea* and *Peudomonas* were incubated at 30° C. Bacteria in the genus *Agrobacterium* and *Zoogloea* were incubated at 26° C. The bacteria were allowed to incubate for 24 to 72 hours without the addition of an additional amount of nutrients. Bacteria in the genus *Agrobacterium, Bacillus, Enterobacter*, and *Peudomonas* were incubated for 24 to 48 hours. Bacteria in the genus *Caulobacter* and *Gordonia* were incubated for 48 to 72 hours. Bacteria were spectroscopically monitored to determine when exponential growth ceases and bacteria have entered the starvation phase.

Example 2

Producing Bacteria-Alginate Particles 40 g of sodium alginate was mixed into an aqueous solution to form solution more viscous than water. The alginate solution was autoclaved at 121° C. for 30 minutes. The alginate solution was then allowed to cool. 500 ml of bacteria in the starvation phase, prepared according to Example 1, was added to the alginate solution to form bacteria-alginate mixture. The bacteria-alginate solution was agitated. The bacteria-alginate solution was added in drops into 2 L of 0.55 M calcium chloride solution. The calcium chloride solution was mixed continuously. Particles, with a length and a width of approximately 5 mm, formed in the calcium chloride solution. The particles were then filtered under at least a partial vacuum using Whatman 40 filter paper, commercially available from Whatman (Middlesex, United Kingdom). The particles were then dried and stored.

Example 3

Producing Bacteria Immobilized on a Hydrophobic Substrate 40 g of sodium alginate was stirred in an aqueous solution. As the solution was stirred, the sodium alginate gelled and became too viscous to stir with a magnetic stir bar. The alginate solution was autoclaved at 121° C. for 30 minutes and then allowed to cool for at least 12 hours. Bacteria, prepared according to Example 1, were incubated with an American Copper Sponge mesh, commercially available from ACS Industries (Woonsocket, R.I.). The bacteria became embedded in the hydrophobic substrate. The bacteria-hydrophobic substrate was placed in the cooled alginate solution and allowed to be saturated with the alginate. The bacteria-alginate-hydrophobic substrate was then added to a solution containing 0.55 M calcium chloride solution. The substrate remained submerged in the calcium chloride solution for 5 minutes. The substrate was then separated from the solution using aseptic techniques. The substrate containing immobilized bacteria was then dried and stored.

Example 4

Contamination Reducing Systems

Bacteria mixture was prepared according to Example 1 containing *Enterobacter cloacae, Pseudomonas putida, Pseudomonas stutzeri, Gordonia* sp., *Bacillus subtilis, Agrobacterium* sp., *Caulobacter vibrioides*, and bacteria in the genus *Zoogloea*.

Figure 12:
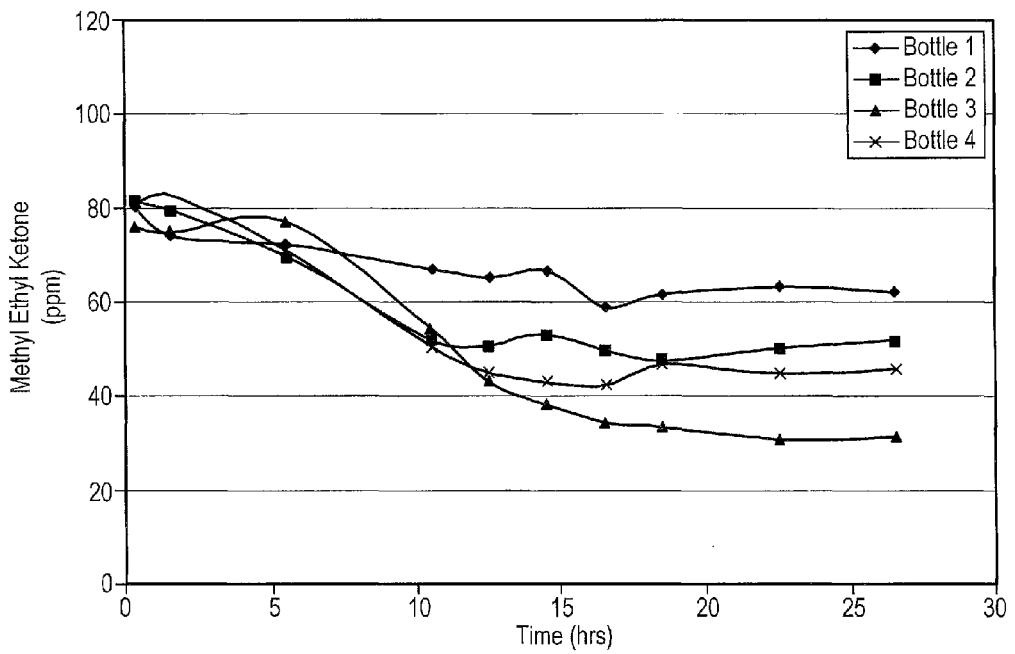
FIG. 12 depicts a graph that shows the change in concentration of methyl ethyl ketone over time in an embodiment of a system for the reduction of contaminants.

A portion of the prepared bacteria mixture was added to a solution containing a substrate, nutrients, and methyl ethyl ketone. FIG. 12 depicts a graph of the concentration of methyl ethyl ketone over time. The bacteria coupled to a substrate reduced the amount of methyl ethyl ketone in the solution.

Figure 13:
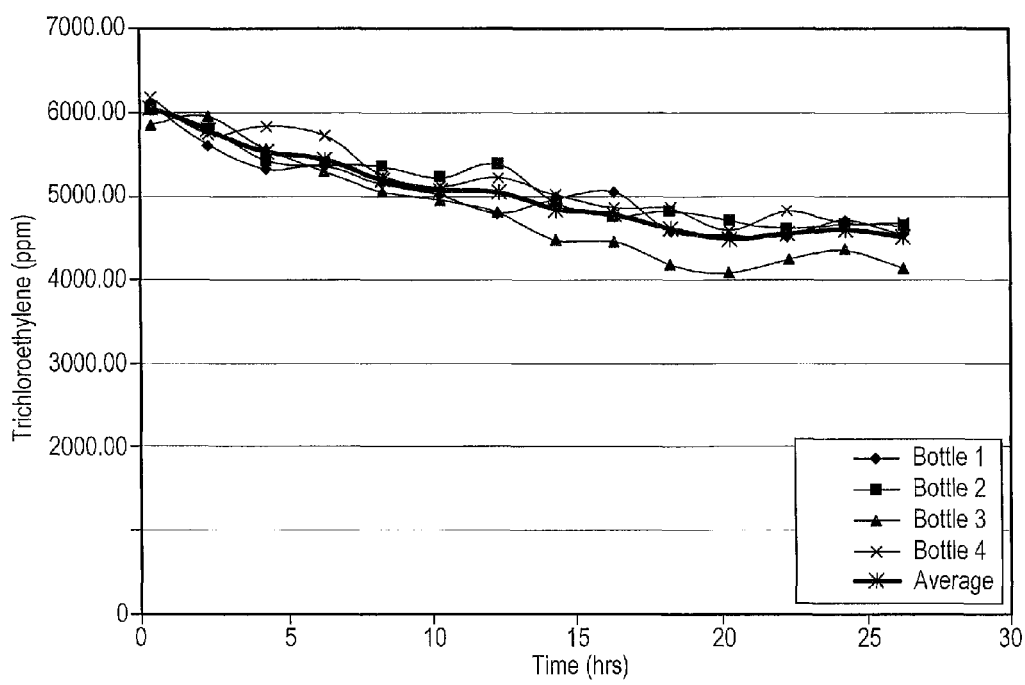
FIG. 13 depicts a graph that shows the change in concentration of trichloroethylene over time in an embodiment of a system for the reduction of contaminants.

A portion of the prepared bacteria mixture was added to a solution containing a substrate, nutrients, and trichloroethylene. As depicted in FIG. 13, trichloroethylene was degraded by a system comprising bacteria coupled to a substrate.

Figure 14:
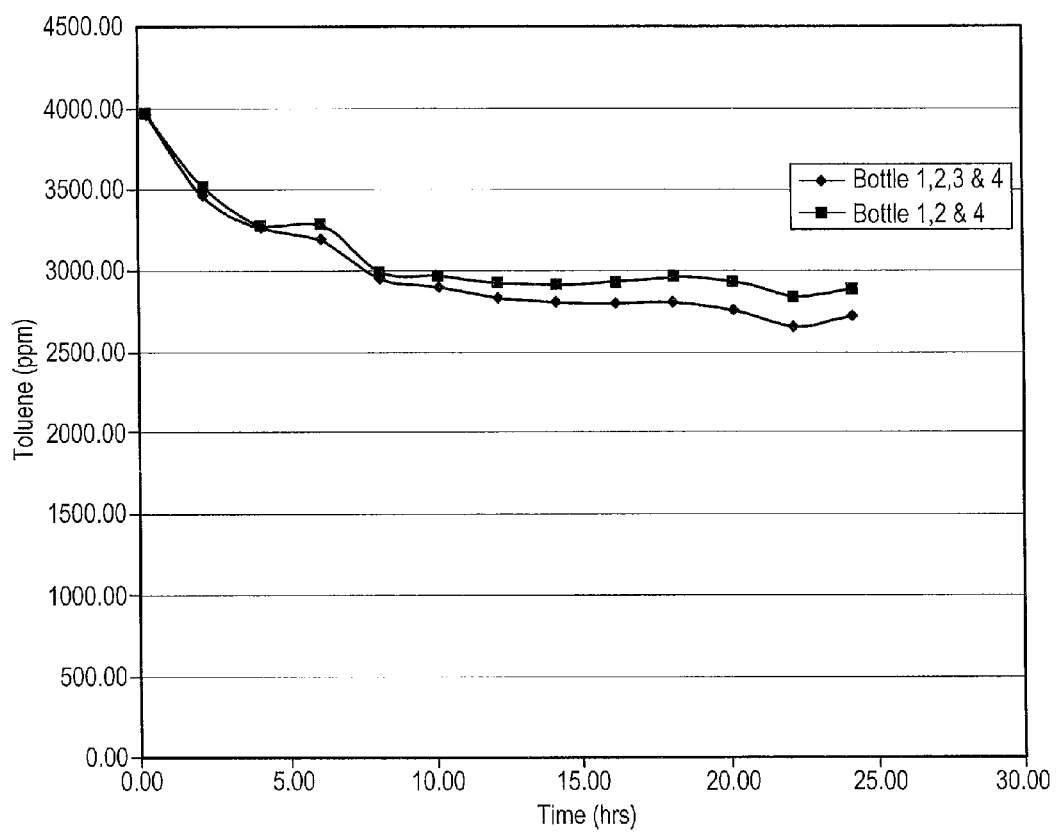
FIG. 14 depicts a graph that shows the change in concentration of toluene over time in an embodiment of a system for the reduction of contaminants.

A portion of the prepared bacteria mixture was added to a solution containing a substrate, nutrients, and toluene. FIG. 14 depicts a graph of the concentration of toluene over time. The bacteria coupled to a substrate reduced the amount of toluene in the solution.

Figure 15:
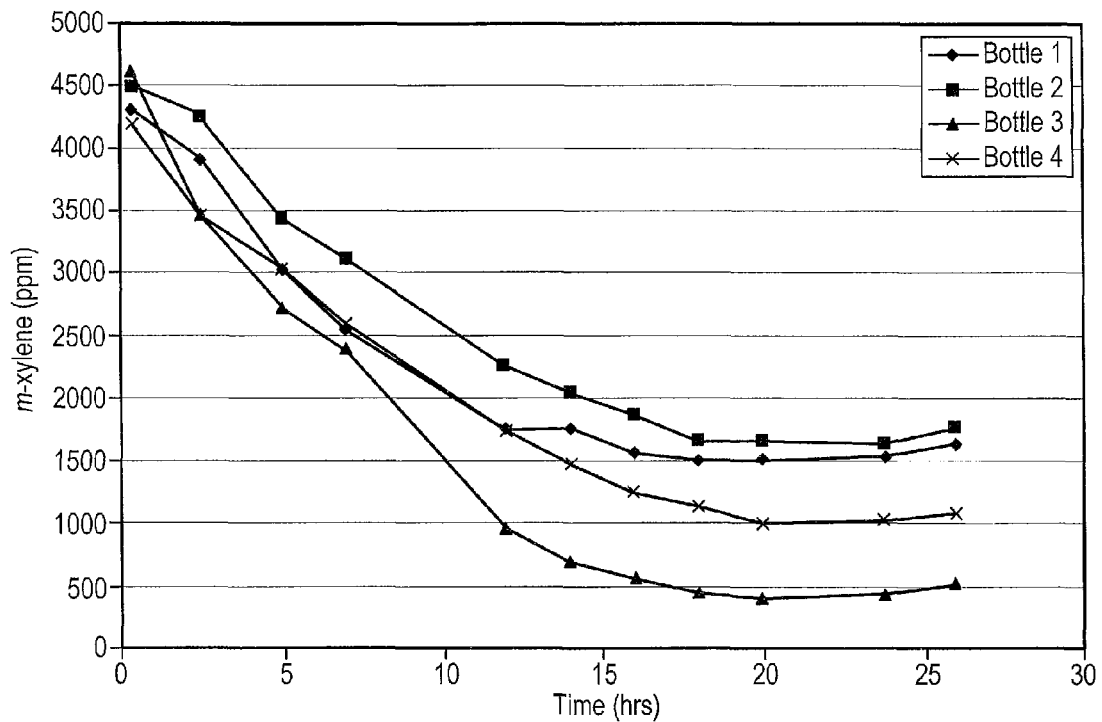
FIG. 15 depicts a graph that shows the change in concentration of m-xylene over time in an embodiment of a system for the reduction of contaminants.

A portion of the prepared bacteria mixture was added to a solution containing a substrate, nutrients, and m-xylene. As depicted in FIG. 15, m-xylene was degraded by a system comprising bacteria coupled to a substrate.

Figure 16:
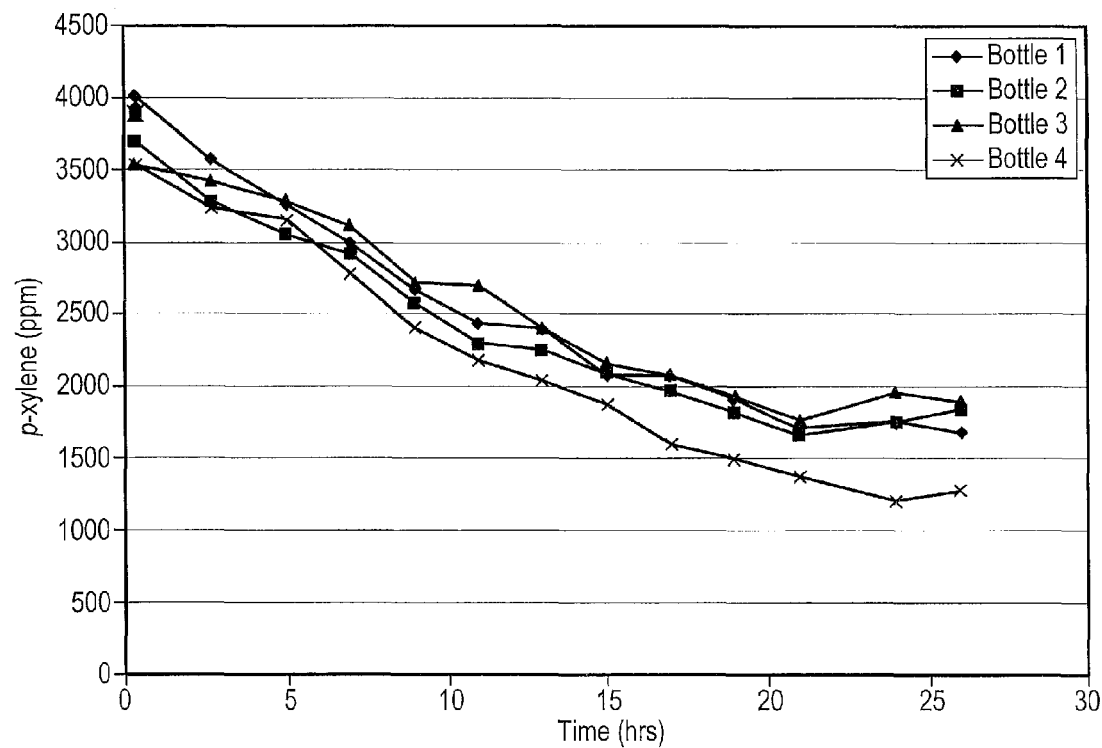
FIG. 16 depicts a graph that shows the change in concentration of p-xylene over time in an embodiment of a system for the reduction of contaminants.

A portion of the prepared bacteria mixture was added to a solution containing a substrate, nutrients, and p-xylene. As depicted in FIG. 16, p-xylene was degraded by a system comprising bacteria coupled to a substrate.

Figure 17:
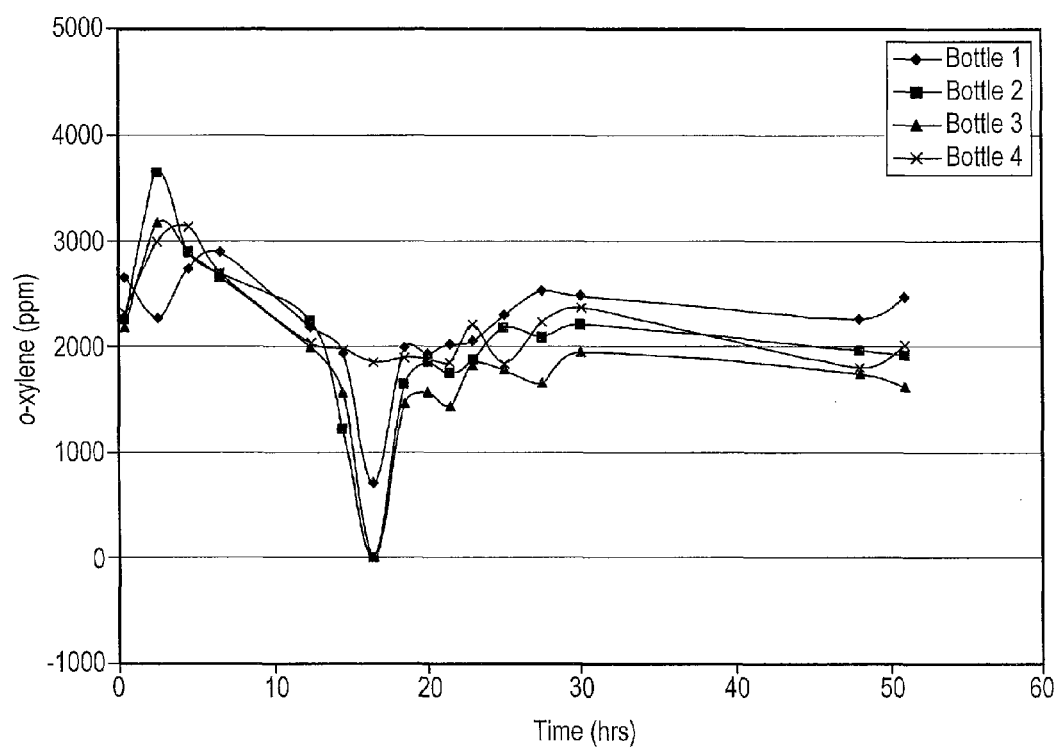
FIG. 17 depicts a graph that shows the change in concentration of o-xylene over time in an embodiment of a system for the reduction of contaminants.

A portion of the prepared bacteria mixture was added to a solution containing a substrate, nutrients, and o-xylene. As depicted in FIG. 17, o-xylene was degraded by a system comprising bacteria coupled to a substrate.

What is claimed is:

1. A system for treatment of wastewater comprising:
   a substrate disposed in a container;
   one or more primary adherer bacteria coupled to the substrate, wherein one or more primary adherer bacteria are capable of coupling to the substrate and one or more other bacteria, and wherein the primary adherer bacteria couple with the substrate such that the primary adherer bacteria are inhibited from being dislodged from the substrate during wastewater treatment;
   one or more secondary adherer bacteria coupled to at least a portion of one or more of the primary adherer bacteria; and
   wherein one or more of the secondary adherer bacteria are capable of reducing contaminants in wastewater while coupled to one or more of the primary adherer bacteria.

2. The system of claim 1, wherein one or more of the substrates are hydrophobic.

3. The system of claim 1, wherein one or more of the substrates are polyethylene.

4. The system of claim 1, wherein at least one of the secondary adherer bacteria comprises bacteria in the genus *Pseudomonas*.

5. The system of claim 1, wherein at least one of the secondary adherer bacteria comprises bacteria in the genus *Bacillus*.

6. The system of claim 1, wherein at least one of the secondary adherer bacteria comprises bacteria in the genus *Agrobacterium*.

7. The system of claim 1, wherein at least one of the secondary adherer bacteria comprises bacteria in the genus *Enterobacter*.

8. The system of claim 1, wherein at least one of the secondary adherer bacteria comprises bacteria in the genus *Zoogloea*.

9. The system of claim 1, wherein at least one of the primary adherer bacteria comprises bacteria in the genus *Gordonia*.

10. The system of claim 1, wherein at least one of the primary adherer bacteria comprises bacteria in the genus *Caulobacter*.

11. The system of claim 1, wherein at least one of the primary adherer bacteria comprises *Caulobacter vibrioides* or *Caulobacter crescentus*.

12. The system of claim 1, wherein the primary adherer bacteria comprises:
    bacteria in the genus *Gordonia*; and
    bacteria in the genus *Caulobacter*.

13. The system of claim 12, wherein the secondary adherer bacteria comprises:
    bacteria in the genus *Pseudomonas;*
    bacteria in the genus *Bacillus;*
    bacteria in the genus *Enterobacter;*
    bacteria in the genus *Zoogloea;* and
    bacteria in the genus *Agrobacterium*.

14. The system of claim 1, wherein the secondary adherer bacteria comprises:
    bacteria in the genus *Pseudomonas;*
    bacteria in the genus *Bacillus;*
    bacteria in the genus *Enterobacter;*
    bacteria in the genus *Zoogloea;* and
    bacteria in the genus *Agrobacterium*.

* * * * *